United States Patent
Inoue et al.

(10) Patent No.: US 9,978,962 B2
(45) Date of Patent: May 22, 2018

(54) ORGANOMETALLIC IRIDIUM COMPLEX, LIGHT-EMITTING ELEMENT, LIGHT-EMITTING DEVICE, ELECTRONIC DEVICE, AND LIGHTING DEVICE

(71) Applicant: Semiconductor Energy Laboratory Co., Ltd., Kanagawa-ken (JP)

(72) Inventors: Hideko Inoue, Kanagawa (JP); Tomoka Hara, Kanagawa (JP); Satoshi Seo, Kanagawa (JP); Toshiki Sasaki, Kanagawa (JP); Kunihiko Suzuki, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 412 days.

(21) Appl. No.: 14/725,332

(22) Filed: May 29, 2015

(65) Prior Publication Data
US 2015/0349278 A1    Dec. 3, 2015

(30) Foreign Application Priority Data
May 30, 2014    (JP) .................. 2014-112278

(51) Int. Cl.
*H01L 51/00*    (2006.01)
*C07F 15/00*    (2006.01)
(Continued)

(52) U.S. Cl.
CPC ...... *H01L 51/0085* (2013.01); *C07F 15/0033* (2013.01); *C09K 11/06* (2013.01);
(Continued)

(58) Field of Classification Search
None
See application file for complete search history.

(56) References Cited

U.S. PATENT DOCUMENTS 7,807,839 B2    10/2010    Inoue et al.
9,048,441 B2    6/2015    Inoue et al.
(Continued)

FOREIGN PATENT DOCUMENTS

| JP | 2007-137872 | 6/2007 |
| JP | 2008-69221 | 3/2008 |
| WO | WO 2008/035664 A1 | 3/2008 |

OTHER PUBLICATIONS

Wang et al. "Synthesis, structure and properties of a novel iridium (III) pyrimidine complex" Inorganic Chemistry Communications 14, 2011, 316-319.*

(Continued)

*Primary Examiner* — Robert S Loewe
(74) *Attorney, Agent, or Firm* — Husch Blackwell LLP

(57) ABSTRACT

To provide a long-lifetime organometallic iridium complex exhibiting yellow light emission with high emission efficiency as a novel substance. The organometallic iridium complex includes a ligand in which an unsubstituted phenyl group is bonded to each of the 2-position and the 5-position of pyrimidine. The organometallic iridium complex has a structure represented by General Formula (G1).

20 Claims, 19 Drawing Sheets

(G1)

(51) Int. Cl.
C09K 11/06 (2006.01)
H05B 33/14 (2006.01)
H01L 51/50 (2006.01)

(52) U.S. Cl.
CPC ...... *H05B 33/14* (2013.01); *C09K 2211/1007* (2013.01); *C09K 2211/1044* (2013.01); *C09K 2211/185* (2013.01); *H01L 51/5016* (2013.01)

(56) References Cited

U.S. PATENT DOCUMENTS

| 2009/0039776 A1* | 2/2009 | Yamada | C07F 15/0033 313/504 |
|---|---|---|---|
| 2013/0165653 A1 | 6/2013 | Inoue et al. | |
| 2015/0073142 A1 | 3/2015 | Ohsawa et al. | |

OTHER PUBLICATIONS

Kozhevnikov et al. "Highly Luminescent Mixed-Metal Pt(II)/Ir(III) Complexes: Bis-Cyclometalation of 4,6-Diphenylpyrimidig As a Versatile Route to Rigid Multimetallic Assemblies" Inorganic Chemistry 2011, 50, 6304-6313.*

* cited by examiner

ORGANOMETALLIC IRIDIUM COMPLEX, LIGHT-EMITTING ELEMENT, LIGHT-EMITTING DEVICE, ELECTRONIC DEVICE, AND LIGHTING DEVICE

BACKGROUND OF THE INVENTION

1. Field of the Invention

One embodiment of the present invention relates to an organometallic iridium complex, particularly, to an organometallic iridium complex that is capable of converting triplet excitation energy into luminescence. In addition, one embodiment of the present invention relates to a light-emitting element, a light-emitting device, an electronic device, and a lighting device each including the organometallic iridium complex. Note that one embodiment of the present invention is not limited to the above technical field. The technical field of one embodiment of the invention disclosed in this specification and the like relates to an object, a method, or a manufacturing method. In addition, one embodiment of the present invention relates to a process, a machine, manufacture, or a composition of matter. Specifically, examples of the technical field of one embodiment of the present invention disclosed in this specification include a semiconductor device, a display device, a liquid crystal display device, a power storage device, a memory device, an imaging device, a method for driving any of them, and a method for manufacturing any of them.

2. Description of the Related Art

Organic compounds are brought into an excited state by the absorption of light. Through this excited state, various reactions (photochemical reactions) are caused in some cases, or luminescence is generated in some cases. Therefore, the organic compounds have a wide range of applications.

As one example of the photochemical reactions, a reaction of singlet oxygen with an unsaturated organic molecule (oxygen addition) is known. Since the ground state of an oxygen molecule is a triplet state, oxygen in a singlet state (singlet oxygen) is not generated by direct photoexcitation. However, in the presence of another triplet excited molecule, singlet oxygen is generated to cause an oxygen addition reaction. In this case, a compound capable of forming the triplet excited molecule is referred to as a photosensitizer.

As described above, for generation of singlet oxygen, a photosensitizer capable of forming a triplet excited molecule by photoexcitation is needed. However, the ground state of an ordinary organic compound is a singlet state; therefore, photoexcitation to a triplet excited state is forbidden transition and generation of a triplet excited molecule is difficult. A compound that can easily cause intersystem crossing from the singlet excited state to the triplet excited state (or a compound that allows the forbidden transition of photoexcitation directly to the triplet excited state) is thus required as such a photosensitizer. In other words, such a compound can be used as the photosensitizer and is useful.

The above compound often exhibits phosphorescence. Phosphorescence refers to luminescence generated by transition between different energies in multiplicity. In an ordinary organic compound, phosphorescence refers to luminescence generated in returning from the triplet excited state to the singlet ground state (in contrast, fluorescence refers to luminescence in returning from the singlet excited state to the singlet ground state). Application fields of a compound capable of exhibiting phosphorescence, that is, a compound capable of converting triplet excitation energy into luminescence (hereinafter, referred to as a phosphorescent compound), include a light-emitting element including an organic compound as a light-emitting substance.

This light-emitting element has a simple structure in which a light-emitting layer including an organic compound that is a light-emitting substance is provided between electrodes. This light-emitting element has attracted attention as a next-generation flat panel display element in terms of characteristics such as being thin and light in weight, high speed response, and direct current low voltage driving. Further, a display device including this light-emitting element is superior in contrast, image quality, and wide viewing angle.

The light-emitting element including an organic compound as a light-emitting substance has a light emission mechanism that is of a carrier injection type: a voltage is applied between electrodes where a light-emitting layer is interposed, electrons and holes injected from the electrodes recombine to put the light-emitting substance into an excited state, and then light is emitted in returning from the excited state to the ground state. As in the case of photoexcitation described above, types of the excited state include a singlet excited state ($S^*$) and a triplet excited state ($T^*$). The statistical generation ratio thereof in the light-emitting element is considered to be $S^*:T^*=1:3$.

At room temperature, a compound capable of converting singlet excitation energy into luminescence (hereinafter, referred to as a fluorescent compound) exhibits only luminescence from the singlet excited state (fluorescence), not luminescence from the triplet excited state (phosphorescence). Accordingly, the internal quantum efficiency (the ratio of the number of generated photons to the number of injected carriers) of a light-emitting element including the fluorescent compound is thought to have a theoretical limit of 25%, on the basis of $S^*:T^*=1:3$.

On the other hand, in a case of a light-emitting element including the phosphorescent compound described above, the internal quantum efficiency thereof can be improved to 75% to 100% in theory; namely, the emission efficiency thereof can be 3 to 4 times as much as that of the light-emitting element including a fluorescent compound. Therefore, the light-emitting element including a phosphorescent compound has been actively developed in recent years in order to achieve a highly efficient light-emitting element. An organometallic complex that contains iridium or the like as a central metal is particularly attracting attention as a phosphorescent compound because of its high phosphorescence quantum yield (refer to Patent Document 1, Patent Document 2, and Patent Document 3).

REFERENCE

Patent Document

[Patent Document 1] Japanese Published Patent Application No. 2007-137872

[Patent Document 2] Japanese Published Patent Application No. 2008-069221

[Patent Document 3] International Publication WO 2008/035664 Pamphlet

SUMMARY OF THE INVENTION

Although phosphorescent materials exhibiting various emission colors have been actively developed as disclosed in Patent Documents 1 to 3, development of novel materials with higher efficiency has been desired.

In view of the above, in one embodiment of the present invention, a novel organometallic iridium complex is provided. A long-lifetime organometallic iridium complex exhibiting yellow light emission with high emission efficiency is provided as a novel substance. A novel organometallic iridium complex that can be used for a light-emitting element is provided. A novel organometallic iridium complex that can be used for an EL layer of a light-emitting element is provided. A light-emitting element using a novel organometallic iridium complex of one embodiment of the present invention is provided. A light-emitting device, an electronic device, and a lighting device each of which includes a light-emitting element using a novel and highly efficient organometallic iridium complex of one embodiment of the present invention are provided. A novel material of one embodiment of the present invention, a novel light-emitting element, a novel light-emitting device, a novel electronic device, or a novel lighting device is provided. Note that the description of these objects does not disturb the existence of other objects. Note that one embodiment of the present invention does not necessarily achieve all the objects listed above. Other objects will be apparent from and can be derived from the description of the specification, the drawings, the claims, and the like.

One embodiment of the present invention is an organometallic iridium complex including a ligand in which a first phenyl group and a second phenyl group are bonded to a pyrimidine ring. Accordingly, one embodiment of the present invention is an organometallic iridium complex having a structure represented by General Formula (G1).

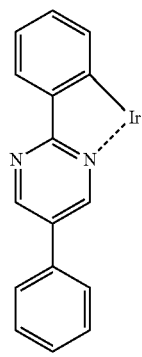

(G1)

Another embodiment of the present invention is an organometallic iridium complex represented by General Formula (G2).

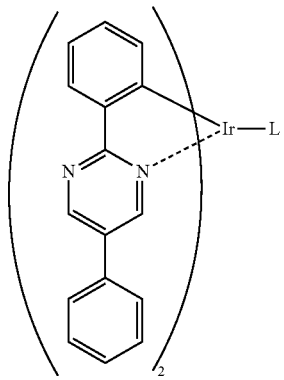

(G2)

In the formula, L represents a monoanionic ligand.
In the above-described structure, the monoanionic ligand is represented by General Formula (L1) or General Formula (L2).

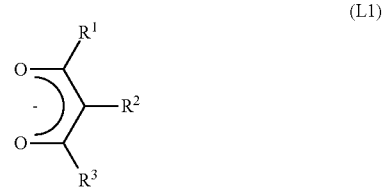

(L1)

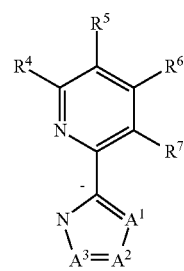

(L2)

In the formulae, each of $R^1$ to $R^7$ individually represents hydrogen, a substituted or unsubstituted alkyl group having 1 to 6 carbon atoms, a halogen group, a vinyl group, a substituted or unsubstituted haloalkyl group having 1 to 6 carbon atoms, a substituted or unsubstituted alkoxy group having 1 to 6 carbon atoms, or a substituted or unsubstituted alkylthio group having 1 to 6 carbon atoms. In addition, each of $A^1$ to $A^3$ independently represents nitrogen, $sp^2$ hybridized carbon bonded to hydrogen, or $sp^2$ hybridized carbon having a substituent. The substituent is an alkyl group having 1 to 6 carbon atoms, a halogen group, a haloalkyl group having 1 to 6 carbon atoms, or a phenyl group.

Another embodiment of the present invention is an organometallic iridium complex represented by Structural Formula (100).

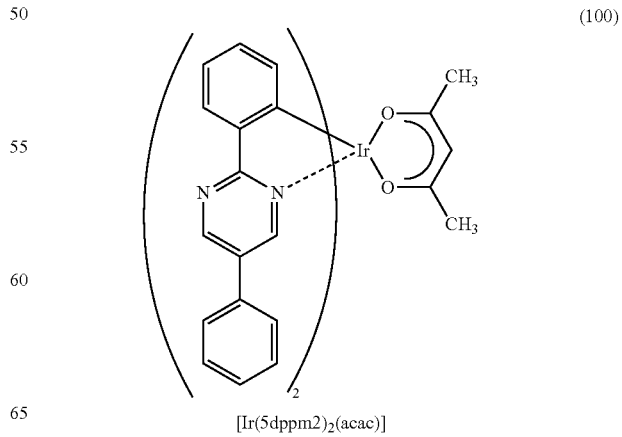

[Ir(5dppm2)$_2$(acac)]

(100)

The organometallic iridium complex of one embodiment of the present invention is a material exhibiting yellow light emission with an emission spectrum having a peak wavelength at around 560 nm (specifically, in the range of 550 nm to 580 nm). The emission spectrum is broad and has a shoulder peak at around 600 nm (specifically, in the range of 570 nm to 630 nm) which is derived from red light emission. In other words, the organometallic iridium complex of one embodiment of the present invention has an emission spectrum having a first peak in the range of 550 nm to 580 nm and a second peak in the range of 570 nm to 630 nm. The emission spectrum of the organometallic iridium complex of one embodiment of the present invention appears at around 500 nm and includes a green light emission component. The light emission maximum is at around 560 nm, which is derived from yellow light emission. The emission spectrum has a shoulder peak at around 600 nm which is derived from red light emission.

The organometallic iridium complex of one embodiment of the present invention is an iridium complex including a ligand in which a first phenyl group and a second phenyl group are bonded to a pyrimidine ring. The first phenyl group is bonded to iridium. The pyrimidine ring forms a coordinate bond with the iridium. The dihedral angle between the pyrimidine ring and the second phenyl group in a stable structure is from −20° to −60° when the organometallic iridium complex is in the singlet ground state ($S_0$). The dihedral angle in a stable structure is from −10° to −50° when the organometallic iridium complex is in the lowest triplet excited state ($T_1$).

In the above structure, the first phenyl group is preferably bonded to the 2-position of the pyrimidine ring. In particular, when the first phenyl group is bonded to the 2-position of the pyrimidine ring and the second phenyl group is bonded to the 5-position of the pyrimidine ring, the dihedral angle has a preferable value.

The organometallic iridium complex of one embodiment of the present invention is very effective for the following reason: the organometallic iridium complex can emit phosphorescence, that is, it can provide luminescence from a triplet excited state and can exhibit emission, and therefore higher efficiency is possible when the organometallic complex is applied to a light-emitting element. Thus, one embodiment of the present invention also includes a light-emitting element in which the organometallic iridium complex of one embodiment of the present invention is used.

Another embodiment of the present invention is a light-emitting device including the above-described light-emitting element and at least one of a transistor and a substrate.

Note that another embodiment of the present invention includes not only a light-emitting device including the light-emitting element but also an electronic device and a lighting device each using the light-emitting device.

Accordingly, another embodiment of the present invention is an electronic device including the light-emitting device and at least one of a microphone, a camera, an operation button, an external connection portion, and a speaker. Another embodiment of the present invention is an electronic device including the light-emitting device and at least one of a housing, a cover, and a support base.

The light-emitting device in this specification refers to an image display device and a light source (e.g., a lighting device). In addition, the light-emitting device includes, in its category, all of a module in which a light-emitting device is connected to a connector such as a flexible printed circuit (FPC), a tape carrier package (TCP), a module in which a printed wiring board is provided on the tip of a TCP, and a module in which an integrated circuit (IC) is directly mounted on a light-emitting element by a chip on glass (COG) method.

One embodiment of the present invention can provide a novel organometallic iridium complex. Another embodiment of the present invention can provide a highly efficient and long-lifetime organometallic iridium complex exhibiting yellow light emission. Another embodiment of the present invention can provide an organometallic iridium complex exhibiting yellow light emission, which includes a ligand in which a first phenyl group and a second phenyl group are bonded to a pyrimidine ring. The first phenyl group is bonded to iridium. The pyrimidine ring forms a coordinate bond with iridium. The organometallic iridium complex has a twist structure where the dihedral angle between the pyrimidine ring and the second phenyl group in a stable structure is from −20° to −60° when the organometallic iridium complex is in the singlet ground state ($S_0$) and from −10° to −50° when the organometallic iridium complex is in the lowest triplet excited state ($T_1$). Another embodiment of the present invention can provide a highly efficient and long-lifetime organometallic iridium complex exhibiting yellow light emission with a broad emission spectrum. The emission spectrum emission appears at around 500 nm which is derived from green light emission, has the light emission maximum at around 560 nm which is derived from yellow light emission, and has a shoulder peak at around 600 nm where is a red light emission region. Another embodiment of the present invention can provide a novel organometallic iridium complex that can be used for a light-emitting element. Another embodiment of the present invention can provide a novel organometallic iridium complex that can be used for an EL layer of a light-emitting element. Another embodiment of the present invention can provide a light-emitting element including the novel organometallic iridium complex of one embodiment of the present invention. Another embodiment of the present invention can provide a light-emitting device, an electronic device, and a lighting device each including a highly efficient light-emitting element including the novel organometallic iridium complex of one embodiment of the present invention. Another embodiment of the present invention can provide a low power consumption light-emitting device, electronic device, or lighting device for which a highly efficient light-emitting element including the novel organometallic iridium complex of one embodiment of the present invention is used. Another embodiment of the present invention can provide a material of one embodiment of the present invention, a novel light-emitting element, a novel light-emitting device, a novel electronic device, or a novel lighting device. Note that the description of these effects does not disturb the existence of other effects. One embodiment of the present invention does not necessarily have all the effects listed above. Other effects will be apparent from and can be derived from the description of the specification, the drawings, the claims, and the like.

DETAILED DESCRIPTION OF THE INVENTION

Figure 1A:
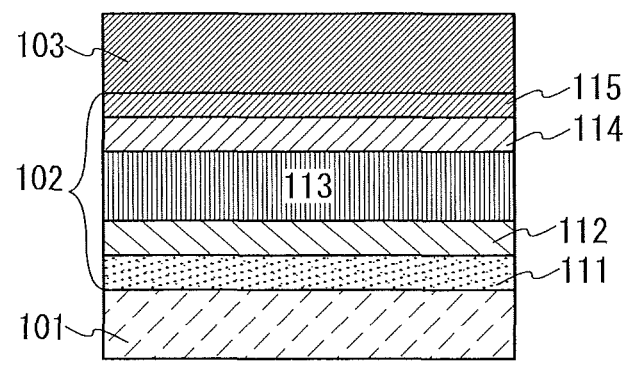
FIGS. 1A and 1B illustrate structures of light-emitting elements.

Hereinafter, embodiments of the present invention will be described with reference to the accompanying drawings. Note that the present invention is not limited to the following description, and modes and details thereof can be variously modified without departing from the spirit and scope of the present invention. Therefore, the present invention should not be construed as being limited to the description in the following embodiments.

Note that the terms "film" and "layer" can be interchanged with each other depending on the case or circumstances. For example, in some cases, the term "conductive film" can be used instead of the term "conductive layer", and the term "insulating layer" can be used instead of the term "insulating film".

Embodiment 1

In this embodiment, an organometallic iridium complex of one embodiment of the present invention is described.

An organometallic iridium complex of one embodiment of the present invention includes a ligand in which an unsubstituted phenyl group is bonded to each of the 2-position and the 5-position of a pyrimidine ring. An organometallic iridium complex of one embodiment of the present invention described in this embodiment has a structure represented by General Formula (G1).

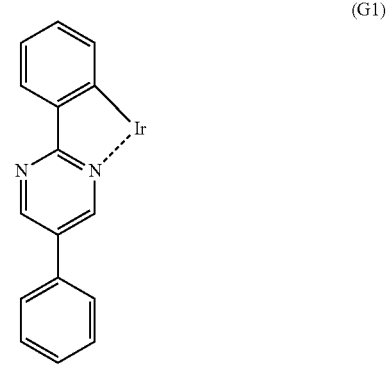

(G1)

An organometallic iridium complex of one embodiment of the present invention described in this embodiment has a structure represented by General Formula (G2).

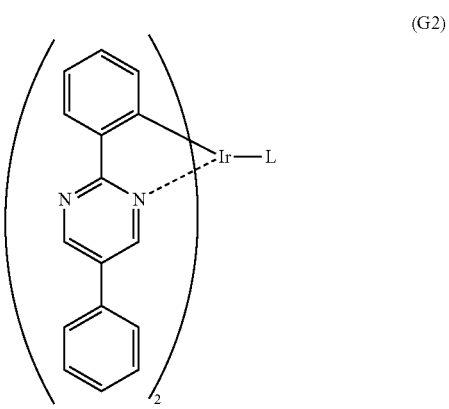

(G2)

In General Formula (G2), L represents a monoanionic ligand.

The monoanionic ligand L in General Formula (G2) is preferably a monoanionic bidentate chelate ligand in which two ligand elements are both oxygen, or a monoanionic bidentate chelate ligand in which two ligand elements are both nitrogen. In particular, it is preferable that the monoanionic ligand L be a monoanionic bidentate chelate ligand in which two ligand elements are both oxygen and have a beta-diketone structure because the beta-diketone structure enhances solubility of an organometallic complex in an organic solvent and makes purification easier. A beta-diketone structure is preferably included to obtain an organometallic complex with high emission efficiency. Furthermore, inclusion of a beta-diketone structure has advantages such as a higher sublimation property and excellent evaporativity.

The monoanionic ligand L in General Formula (G2) is preferably represented by General Formula (L1) or General Formula (L2). Since these ligands have high coordinative ability and can be obtained at low price, they are useful.

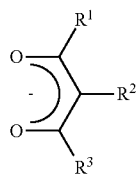
(L1)

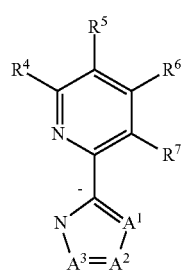
(L2)

In General Formula (L1) or (L2), each of $R^1$ to $R^7$ individually represents hydrogen, a substituted or unsubstituted alkyl group having 1 to 6 carbon atoms, a halogen group, a vinyl group, a substituted or unsubstituted haloalkyl group having 1 to 6 carbon atoms, a substituted or unsubstituted alkoxy group having 1 to 6 carbon atoms, or a substituted or unsubstituted alkylthio group having 1 to 6 carbon atoms. In addition, each of $A^1$ to $A^3$ independently represents nitrogen, $sp^2$ hybridized carbon bonded to hydrogen, or $sp^2$ hybridized carbon having a substituent. The substituent is an alkyl group having 1 to 6 carbon atoms, a halogen group, a haloalkyl group having 1 to 6 carbon atoms, or a phenyl group.

Next, specific structural formulae of the above-described organometallic iridium complexes, each of which is one embodiment of the present invention, are shown (Structural Formulae (100) to (109)). Note that the present invention is not limited thereto.

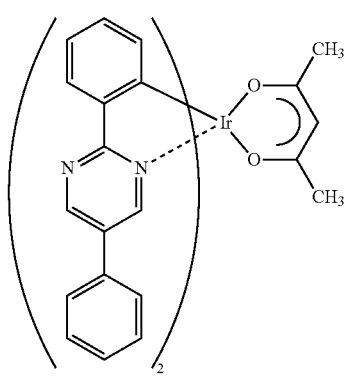
(100)

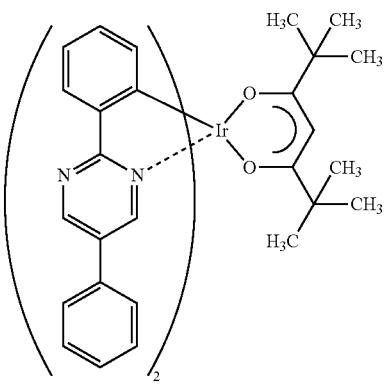
(101)

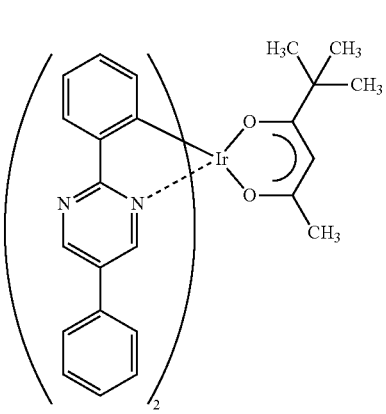
(102)

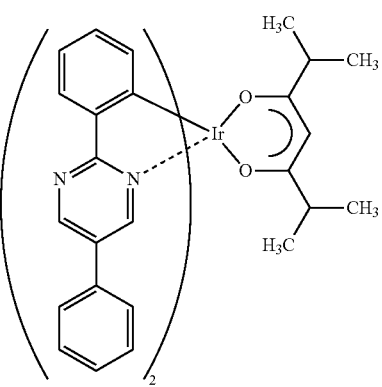
(103)

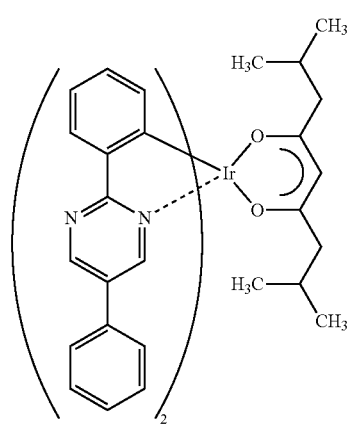
(104)

-continued (105)

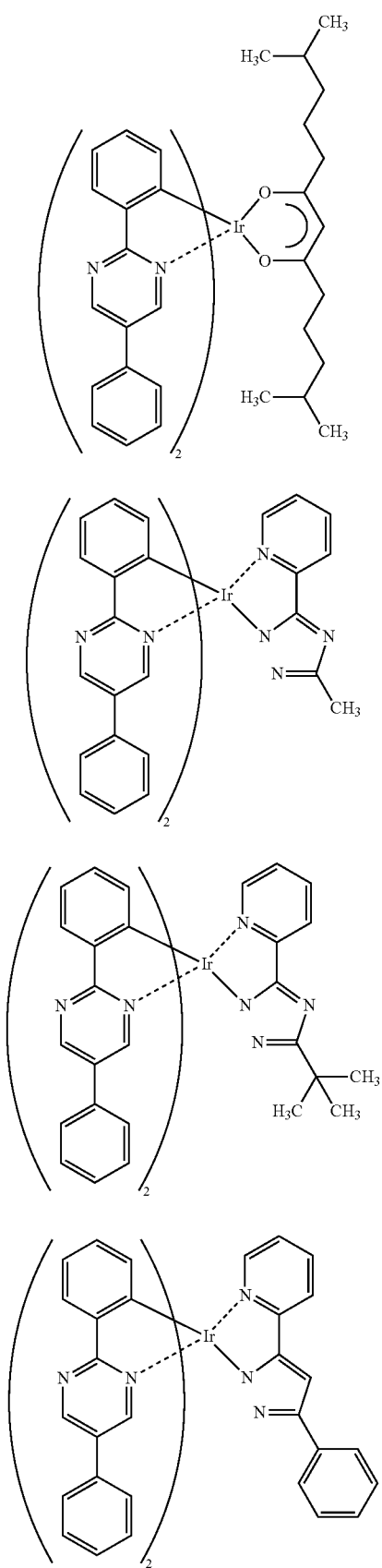

(106)

(107)

(108)

-continued (109)

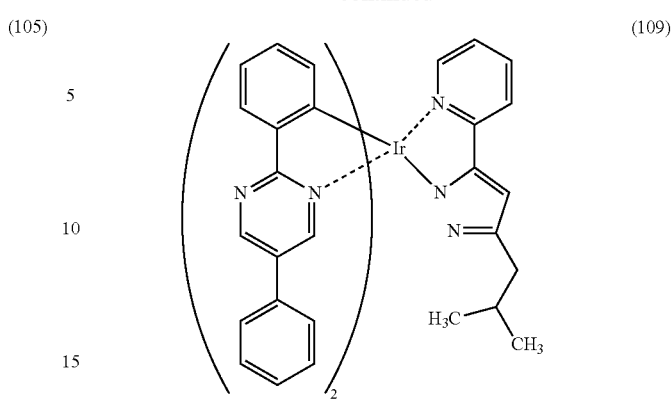

Note that organometallic iridium complexes represented by Structural Formulae (100) to (109) are novel substances capable of emitting phosphorescence. Note that there can be geometrical isomers and stereoisomers of these substances depending on the type of the ligand. The organometallic iridium complex of one embodiment of the present invention includes all of these isomers.

Next, an example of a method for synthesizing the organometallic iridium complex represented by General Formula (G2) is described.

<<Synthesis Method of Organometallic Complex of One Embodiment of the Present Invention Represented by General Formula (G2)>>

As shown in Synthesis Scheme (A-1), a pyrimidine derivative represented by General Formula (G0) and an iridium compound which contains a halogen (e.g., iridium chloride, iridium bromide, or iridium iodide) are heated in an inert gas atmosphere by using no solvent, an alcohol-based solvent (e.g., glycerol, ethylene glycol, 2-methoxyethanol, or 2-ethoxyethanol) alone, or a mixed solvent of water and one or more of the alcohol-based solvents, whereby a dinuclear complex (P), which is one type of an organometallic complex including a halogen-bridged structure, can be obtained. There is no particular limitation on a heating means, and an oil bath, a sand bath, or an aluminum block may be used. Alternatively, microwaves can be used as a heating means.

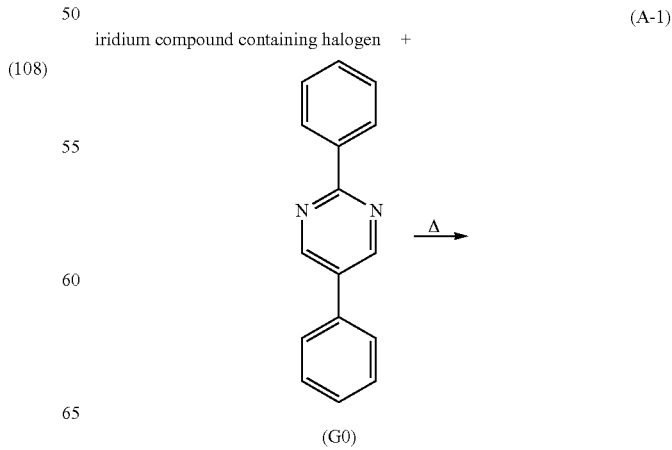

(A-1)

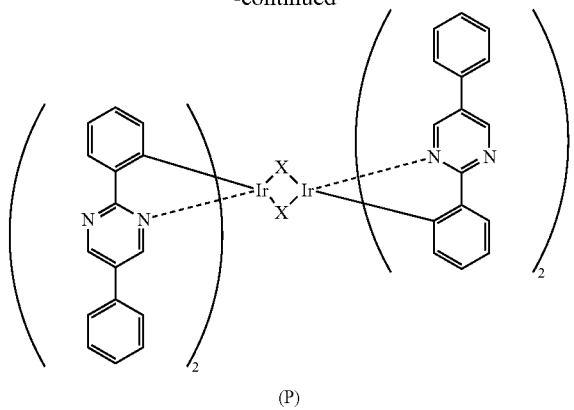

(P)

In Synthesis Scheme (A-1), X represents halogen.

Furthermore, as shown in Synthesis Scheme (A-2), the dinuclear complex (P) obtained in Synthesis Scheme (A-1) is reacted with HL which is a material of a monoanionic ligand in an inert gas atmosphere, whereby a proton of HL is separated and L coordinates to the central metal, iridium. Thus, the organometallic complex of one embodiment of the present invention which is represented by General Formula (G2) can be obtained. There is no particular limitation on a heating means, and an oil bath, a sand bath, or an aluminum block may be used. Alternatively, microwaves can be used as a heating means.

(A-2)

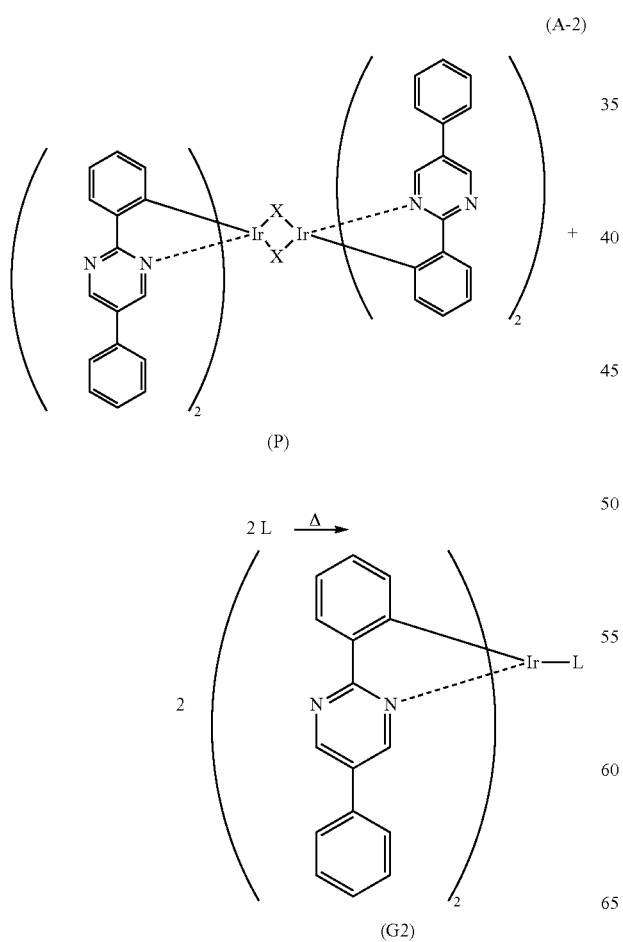

(G2)

In Synthesis Scheme (A-2), L represents a monoanionic ligand and X represents halogen.

The above is the description of the example of a method for synthesizing an organometallic iridium complex of one embodiment of the present invention; however, the present invention is not limited thereto and any other synthesis method may be employed.

The organometallic iridium complex of one embodiment of the present invention is a material exhibiting yellow light emission with an emission spectrum having a peak wavelength at around 560 nm (specifically, in the range of 550 nm to 580 nm). The emission spectrum is broad and has a shoulder peak at around 600 nm (specifically, in the range of 570 nm to 630 nm) which is derived from red light emission. In other words, the organometallic iridium complex of one embodiment of the present invention has an emission spectrum having a first peak in the range of 550 nm to 580 nm and a second peak in the rage of 570 nm to 630 nm. The emission spectrum of the organometallic iridium complex of one embodiment of the present invention appears at around 500 nm and includes a green light emission component. The light emission maximum is at around 560 nm, which is derived from yellow light emission. The emission spectrum has a shoulder peak at around 600 nm which is derived from red light emission.

The above-described organometallic iridium complex of one embodiment of the present invention can emit phosphorescence and thus can be used as a light-emitting material or a light-emitting substance of a light-emitting element.

With the use of the organometallic iridium complex of one embodiment of the present invention, a light-emitting element, a light-emitting device, an electronic device, or a lighting device with high emission efficiency can be obtained. Alternatively, it is possible to obtain a light-emitting element, a light-emitting device, an electronic device, or a lighting device with low power consumption.

The structure described in this embodiment can be combined as appropriate with any of the structures described in the other embodiments.

Embodiment 2

In this embodiment, a light-emitting element in which the organometallic iridium complex of one embodiment of the present invention can be used as an EL material is described with reference to FIGS. 1A and 1B.

In a light-emitting element described in this embodiment, as illustrated in FIG. 1A, an EL layer 102 including a light-emitting layer 113 is interposed between a pair of electrodes (a first electrode (anode) 101 and a second electrode (cathode) 103), and the EL layer 102 includes a hole-injection layer 111, a hole-transport layer 112, an electron-transport layer 114, an electron-injection layer 115, and the like in addition to the light-emitting layer 113.

When voltage is applied to such a light-emitting element, holes injected from the first electrode 101 side and electrons injected from the second electrode 103 side recombine in the light-emitting layer 113 to raise a light-emitting substance contained in the light-emitting layer 113 to an excited state. The light-emitting substance in the excited state emits light when it returns to the ground state. The organometallic iridium complex of one embodiment of the present invention can be used as a light-emitting substance in a light-emitting element.

The organometallic iridium complex of one embodiment of the present invention can be used for any one or more layers in the EL layer 102 described in this embodiment. In particular, the organometallic iridium complex is preferably used for the light-emitting layer 113. In other words, the organometallic iridium complex is used in part of a light-emitting element having a structure described below.

A preferred specific example in which the light-emitting element described in this embodiment is fabricated is described below.

As the first electrode (anode) 101 and the second electrode (cathode) 103, a metal, an alloy, an electrically conductive compound, a mixture thereof, and the like can be used. Specific examples are indium oxide-tin oxide (indium tin oxide (ITO)), indium oxide-tin oxide containing silicon or silicon oxide, indium oxide-zinc oxide (indium zinc oxide), indium oxide containing tungsten oxide and zinc oxide, gold (Au), platinum (Pt), nickel (Ni), tungsten (W), chromium (Cr), molybdenum (Mo), iron (Fe), cobalt (Co), copper (Cu), palladium (Pd), and titanium (Ti). In addition, an element belonging to Group 1 or Group 2 of the periodic table, for example, an alkali metal such as lithium (Li) or cesium (Cs), an alkaline earth metal such as calcium (Ca) or strontium (Sr), magnesium (Mg), an alloy containing such an element (MgAg or AlLi), a rare earth metal such as europium (Eu) or ytterbium (Yb), an alloy containing such an element, graphene, and the like can be used. The first electrode (anode) 101 and the second electrode (cathode) 103 can be formed by, for example, a sputtering method or an evaporation method (including a vacuum evaporation method).

The hole-injection layer 111 injects holes into the light-emitting layer 113 through the hole-transport layer 112 having a high hole-transport property. The hole-injection layer 111 contains a substance having a high hole-transport property and an acceptor substance, so that electrons are extracted from the substance having a high hole-transport property by the acceptor substance to generate holes and the holes are injected into the light-emitting layer 113 through the hole-transport layer 112. The hole-transport layer 112 is formed using a substance having a high hole-transport property.

Specific examples of the substance having a high hole-transport property, which is used for the hole-injection layer 111 and the hole-transport layer 112, include aromatic amine compounds such as 4,4'-bis[N-(1-naphthyl)-N-phenylamino]biphenyl (abbreviation: NPB or a-NPD), N,N'-bis(3-methylphenyl)-N,N'-diphenyl-[1,1'biphenyl]-4,4'-diamine (abbreviation: TPD), 4,4',4"-tris(carbazol-9-yl)triphenylamine (abbreviation: TCTA), 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), and 4,4'-bis[N-(spiro-9,9'-bifluoren-2-yl)-N-phenylamino]biphenyl (abbreviation: BSPB); 3-[N-(9-phenylcarbazol-3-yl)-N-phenylamino]-9-phenylcarbazole (abbreviation: PCzPCA1); 3,6-bis[N-(9-phenylcarbazol-3-yl)-N-phenylamino]-9-phenylcarbazole (abbreviation: PCzPCA2); and 3-[N-(1-naphthyl)-N-(9-phenylcarbazol-3-yl)amino]-9-phenylcarbazole (abbreviation: PCzPCN1). Other examples include carbazole derivatives such as 4,4'-di(N-carbazolyl)biphenyl (abbreviation: CBP), 1,3,5-tris[4-(N-carbazolyl)phenyl]benzene (abbreviation: TCPB), and 9-[4-(10-phenyl-9-anthracenyl)phenyl]-9H-carbazole (abbreviation: CzPA). The substances listed here are mainly ones that have a hole mobility of $1 \times 10^{-6}$ cm$^2$/Vs or higher. Note that any substance other than the substances listed here may be used as long as the hole-transport property is higher than the electron-transport property.

A high molecular compound such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), or poly[N,N'-bis(4-butylphenyl)-N,N'-bis(phenyl)benzidine] (abbreviation: Poly-TPD) can also be used.

Examples of the acceptor substance that is used for the hole-injection layer 111 include oxides of metals belonging to Groups 4 to 8 of the periodic table. Specifically, molybdenum oxide is particularly preferable.

The light-emitting layer 113 is a layer containing a light-emitting substance. The light-emitting layer 113 may contain only a light-emitting substance; alternatively, an emission center substance (guest material) may be dispersed in a host material in the light-emitting layer 113. Note that as the host material, the above-described substance having a high hole-transport property or a later-described substance having a high electron-transport property can be used, and preferably, a substance having high triplet excitation energy is used. Accordingly, the organometallic iridium complex of one embodiment of the present invention described in Embodiment 1 may be used as a light-emitting substance in combination with a host material.

The materials that can be used as the light-emitting substance and the emission center substance in the light-emitting layer 113 are not limited to the organometallic iridium complex of one embodiment of the present invention. For example, a light-emitting substance converting singlet excitation energy into luminescence or a light-emitting substance converting triplet excitation energy into luminescence can be used in combination. Described below are examples of the light-emitting substance and the emission center substance.

As an example of the light-emitting substance converting singlet excitation energy into luminescence, a substance emitting fluorescence can be given.

Examples of the substance emitting fluorescence include N,N'-bis[4-(9H-carbazol-9-yl)phenyl]-N,N'-diphenylstilbene-4,4'-diamine (abbreviation: YGA$^2$S), 4-(9H-carbazol-9-yl)-4'-(10-phenyl-9-anthryl)triphenylamine (abbreviation: YGAPA), 4-(9H-carbazol-9-yl)-4'-(9,10-diphenyl-2-anthryl)triphenylamine (abbreviation: 2YGAPPA), N,9-diphenyl-N-[4-(10-phenyl-9-anthryl)phenyl]-9H-carbazol-3-amine (abbreviation: PCAPA), perylene, 2,5,8,11-tetra(tert-butyl)perylene (abbreviation: TBP), 4-(10-phenyl-9-anthryl)-4'-(9-phenyl-9H-carbazol-3-yl)triphenylamine (abbreviation: PCBAPA), N,N"-(2-tert-butylanthracene-9,10-diyldi-4,1-phenylene)bis[N,N',N'-triphenyl-1,4-phenylenediamine] (abbreviation: DPABPA), N,9-diphenyl-N-[4-(9,10-diphenyl-2-anthryl)phenyl]-9H-carbazol-3-amine (abbreviation: 2PCAPPA), N-[4-(9,10-diphenyl-2-anthryl)phenyl]-N,N',N'-triphenyl-1,4-phenylenediamine (abbreviation: 2DPAPPA), N,N,N',N',N",N",N"',N"'-octaphenyldibenzo[g,p]chrysene-2,7,10,15-tetraamine (abbreviation: DBC1), coumarin 30, N-(9, 10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), 9,10-bis(1,1'-biphenyl-2-yl)-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), coumarin 545T, N,N'-diphenylquinacridone (abbreviation: DPQd), rubrene, 5,12-bis(1,1'-biphenyl-4-yl)-6,11-diphenyltetracene (abbreviation: BPT), 2-(2-{2-[4-(dimethylamino)phenyl]ethenyl}-6-methyl-4H-pyran-4-ylidene)propanedinitrile (abbreviation: DCM1), 2-{2-methyl-6-[2-(2,3,6,7-tetrahydro-1H,5H-benzo[ij]quinolizin-9-yl)ethenyl]-4H-pyran-4-ylidene}propanedinitrile (abbreviation: DCM2), N,N,N',N'-tetrakis(4-methylphenyl)tetracene-5,11-diamine (abbreviation: p-mPhTD), 7,14-diphenyl-N,N,N',N'-tetrakis(4-methylphenyl)acenaphtho[1,2-a]fluoranthene-3,10-diamine (abbreviation: p-mPhAFD), {2-isopropyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTI), {2-tert-butyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTB), 2-(2,6-bis{2-[4-(dimethylamino)phenyl]ethenyl}-4H-pyran-4-ylidene)propanedinitrile (abbreviation: BisDCM), and 2-{2,6-bis[2-(8-methoxy-1,1,7,7-tetramethyl-2,3,6,7-tetrahydro-1H,5H-benzo[ij]quinolizin-9-yl)ethenyl]-4H-pyran-4-ylidene}propanedinitrile (abbreviation: BisDCJTM).

Examples of the light-emitting substance converting triplet excitation energy into luminescence include a substance emitting phosphorescence and a thermally activated delayed fluorescence (TADF) material. Note that "delayed fluorescence" exhibited by the TADF material refers to light emission having the same spectrum as normal fluorescence and an extremely long lifetime. The lifetime is $10^{-6}$ seconds or longer, preferably $10^{-3}$ seconds or longer.

Examples of the substance emitting phosphorescence include bis{2-[3',5'-bis(trifluoromethyl)phenyl]pyridinato-N,$C^{2'}$}iridium(III)picolinate (abbreviation: Ir($CF_3$ppy)$_2$(pic)), bis[2-(4',6'-difluorophenyl)pyridinato-N,$C^{2'}$]iridium(III)acetylacetonate (abbreviation: FIracac), tris(2-phenylpyridinato)iridium(III) (abbreviation: Ir(ppy)$_3$), bis(2-phenylpyridinato)iridium(III)acetylacetonate (abbreviation: Ir(ppy)$_2$(acac)), tris(acetylacetonato)(monophenanthroline)terbium(III) (abbreviation: Tb(acac)$_3$(Phen)), bis(benzo[h]quinolinato)iridium(III)acetylacetonate (abbreviation: Ir(bzq)$_2$(acac)), bis(2,4-diphenyl-1,3-oxazolato-N,$C^{2'}$)iridium(III)acetylacetonate (abbreviation: Ir(dpo)$_2$(acac)), bis{2-[4'-(perfluorophenyl)phenyl]pyridinato-N,$C^{2'}$}iridium(III)acetylacetonate (abbreviation: Ir(p-PF-ph)$_2$(acac)), bis(2-phenylbenzothiazolato-N,$C^{2'}$)iridium(III)acetylacetonate (abbreviation: Ir(bt)$_2$(acac)), bis[2-(2'-benzo[4,5-a]thienyl)pyridinato-N,$C^{3'}$]iridium(III)acetylacetonate (abbreviation: Ir(btp)$_2$(acac)), bis(1-phenylisoquinolinato-N,$C^{2'}$)iridium(III)acetylacetonate (abbreviation: Ir(piq)$_2$(acac)), (acetylacetonato)bis[2,3-bis(4-fluorophenyl)quinoxalinato]iridium(III) (abbreviation: Ir(Fdpq)$_2$(acac)), (acetylacetonato)bis(3,5-dimethyl-2-phenylpyrazinato)iridium(III) (abbreviation: [Ir(mppr-Me)$_2$(acac)]), (acetylacetonato)bis(5-isopropyl-3-methyl-2-phenylpyrazinato)iridium(III) (abbreviation: [Ir(mppr-iPr)$_2$(acac)]), (acetylacetonato)bis(2,3,5-triphenylpyrazinato)iridium(III) (abbreviation: Ir(tppr)$_2$(acac)), bis(2,3,5-triphenylpyrazinato)(dipivaloylmethanato)iridium(III) (abbreviation: [Ir(tppr)$_2$(dpm)], (acetylacetonato)bis(6-tert-butyl-4-phenylpyrimidinato)iridium(III) (abbreviation: [Ir(tBuppm)$_2$(acac)]), (acetylacetonato)bis(4,6-diphenylpyrimidinato)iridium(III) (abbreviation: [Ir(dppm)$_2$(acac)]), 2,3,7,8,12,13,17,18-octaethyl-21H,23H-porphyrin platinum (II) (abbreviation: PtOEP), tris(1,3-diphenyl-1,3-propanedionato)(monophenanthroline)europium(III) (abbreviation: Eu(DBM)$_3$(Phen)), and tris[1-(2-thenoyl)-3,3,3-trifluoroacetonato](monophenanthroline)europium(III) (abbreviation: Eu(TTA)$_3$(Phen)).

Preferable examples of the substance (i.e., host material) used for dispersing the light-emitting substance converting triplet excitation energy into luminescence include compounds having an arylamine skeleton, such as 2,3-bis(4-diphenylaminophenyl)quinoxaline (abbreviation: TPAQn) and NPB, carbazole derivatives such as CBP and 4,4',4"-tris(carbazol-9-yl)triphenylamine (abbreviation: TCTA), and metal complexes such as bis[2-(2-hydroxyphenyl)pyridinato]zinc (abbreviation: Znpp$_2$), bis[2-(2-hydroxyphenyl)benzoxazolato]zinc (abbreviation: Zn(BOX)$_2$), bis(2-methyl-8-quinolinolato)(4-phenylphenolato)aluminum (abbreviation: BAlq), and tris(8-quinolinolato)aluminum (abbreviation: Alq$_3$). Alternatively, a high molecular compound such as PVK can be used.

Examples of the TADF material includes fullerene, a derivative thereof, an acridine derivative such as proflavine, and eosin. Other examples include a metal-containing porphyrin, such as a porphyrin containing magnesium (Mg), zinc (Zn), cadmium (Cd), tin (Sn), platinum (Pt), indium (In), or palladium (Pd). Examples of the metal-containing porphyrin include a protoporphyrin-tin fluoride complex (SnF$_2$(Proto IX)), a mesoporphyrin-tin fluoride complex (SnF$_2$(Meso IX)), a hematoporphyrin-tin fluoride complex (SnF$_2$(Hemato IX)), a coproporphyrin tetramethyl ester-tin fluoride complex (SnF$_2$(Copro III-4Me)), an octaethylporphyrin-tin fluoride complex (SnF$_2$(OEP)), an etioporphyrin-tin fluoride complex (SnF$_2$(Etio I)), and an octaethylporphyrin-platinum chloride complex (PtCl$_2$OEP). Alternatively, a heterocyclic compound including a π-electron rich heteroaromatic ring and a π-electron deficient heteroaromatic ring can be used, such as 2-(biphenyl-4-yl)-4,6-bis(12-phenylindolo[2,3-a]carbazol-11-yl)-1,3,5-triazine (PIC-TRZ). Note that a material in which the π-electron rich heteroaromatic ring is directly bonded to the π-electron deficient heteroaromatic ring is particularly preferably used because both the donor property of the π-electron rich heteroaromatic ring and the acceptor property of the π-electron deficient heteroaromatic ring are increased and the energy difference between the S1 level and the T1 level becomes small.

When the light-emitting layer 113 includes one or more kinds of host materials and a light-emitting substance converting singlet excitation energy into luminescence or any of the light-emitting substances converting triplet excitation energy into luminescence (i.e., a guest material), light emission with high emission efficiency can be obtained from the light-emitting layer 113. When two or more kinds of host materials are used, they are preferably a combination which can form an exciplex.

Figure 1B:
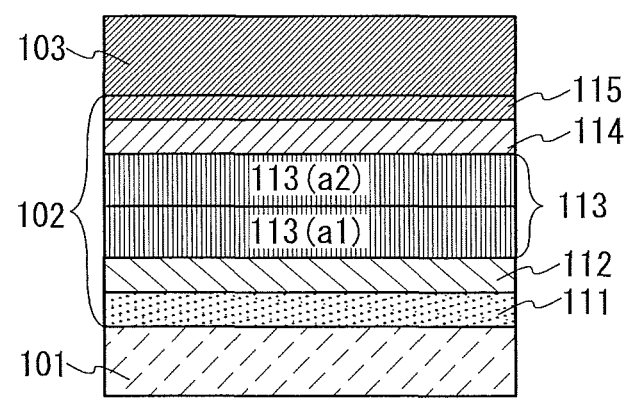

The light-emitting layer 113 may have a stacked structure as illustrated in FIG. 1B. In that case, each layer in the stacked structure emits light. For example, fluorescence is obtained from a first light-emitting layer 113(a1) in the stacked structure, and phosphorescence is obtained from a second light-emitting layer 113(a2) stacked over the first layer. Note that the stacking order may be reversed. It is preferable that light emission due to energy transfer from an excited complex to a dopant be obtained from the layer that emits phosphorescence. In the case where blue light emission is obtained from one of the first and second layers, orange or yellow light emission can be obtained from the other layer. Each layer may contain various kinds of dopants.

The electron-transport layer 114 is a layer containing a substance having a high electron-transport property. For the electron-transport layer 114, a metal complex such as tris(8-quinolinolato)aluminum (abbreviation: Alq$_3$), tris(4-methyl-8-quinolinolato)aluminum (abbreviation: Almq$_3$), bis(10-hydroxybenzo[h]quinolinato)beryllium (abbreviation: BeBq$_2$), bis(2-methyl-8-quinolinolato)(4-phenylphenolato)aluminum (abbreviation: BAlq), bis[2-(2-hydroxyphenyl)benzoxazolato]zinc (abbreviation: Zn(BOX)$_2$), or bis[2-(2-hydroxyphenyl)benzothiazolato]zinc (abbreviation: Zn(BTZ)$_2$) can be used. Alternatively, a heteroaromatic compound such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4'-tert-butylphenyl)-4-phenyl-5-(4"-biphenyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: Bphen), bathocuproine (abbreviation: BCP), or 4,4'-bis(5-methylbenzoxazol-2-yl)stilbene (abbreviation: BzOs) can also be used. A high molecular compound such as poly(2,5-pyridinediyl) (abbreviation: PPy), poly[(9,9-dihexylfluorene-2,7-diyl)-co-(pyridine-3,5-diyl)] (abbreviation: PF-Py) or poly[(9,9-dioctylfluorene-2,7-diyl)-co-(2,2'-bipyridine-6,6'-diyl)] (abbreviation: PF-BPy) can also be used. The substances listed here are mainly ones that have an electron mobility of $1 \times 10^{-6}$ cm$^2$/Vs or higher. Note that any substance other than the substances listed here may be used for the electron-transport layer 114 as long as the electron-transport property is higher than the hole-transport property.

The electron-transport layer 114 is not limited to a single layer, but may be a stack of two or more layers each containing any of the substances listed above.

The electron-injection layer 115 is a layer containing a substance having a high electron-injection property. For the electron-injection layer 115, an alkali metal, an alkaline earth metal, or a compound thereof, such as lithium fluoride (LiF), cesium fluoride (CsF), calcium fluoride (CaF$_2$), or lithium oxide (LiO$_x$) can be used. A rare earth metal compound like erbium fluoride (ErF$_3$) can also be used. An electride may also be used for the electron-injection layer 115. Examples of the electride include a substance in which electrons are added at high concentration to calcium oxide-aluminum oxide. Any of the substances for forming the electron-transport layer 114, which are given above, can be used.

A composite material in which an organic compound and an electron donor (donor) are mixed may also be used for the electron-injection layer 115. Such a composite material is excellent in an electron-injection property and an electron-transport property because electrons are generated in the organic compound by the electron donor. In this case, the organic compound is preferably a material that is excellent in transporting the generated electrons. Specifically, for example, the substances for forming the electron-transport layer 114 (e.g., a metal complex or a heteroaromatic compound), which are given above, can be used. As the electron donor, a substance showing an electron-donating property with respect to the organic compound may be used. Specifically, an alkali metal, an alkaline earth metal, and a rare earth metal are preferable, and lithium, cesium, magnesium, calcium, erbium, and ytterbium are given. In addition, an alkali metal oxide or an alkaline earth metal oxide is preferable, and lithium oxide, calcium oxide, and barium oxide are given. A Lewis base such as magnesium oxide can also be used. An organic compound such as tetrathiafulvalene (abbreviation: TTF) can also be used.

Note that each of the above-described hole-injection layer 111, hole-transport layer 112, light-emitting layer 113, electron-transport layer 114, and electron-injection layer 115 can be formed by a method such as an evaporation method (e.g., a vacuum evaporation method), an ink-jet method, or a coating method.

In the above-described light-emitting element, holes and electrons are recombined in the EL layer 102, whereby light is emitted. Then, the emitted light is extracted outside through one or both of the first electrode 101 and the second electrode 103. Thus, one or both of the first electrode 101 and the second electrode 103 are electrodes having light-transmitting properties.

Note that the light-emitting element described in this embodiment is an example of a light-emitting element formed using the organometallic iridium complex of one embodiment of the present invention as an EL material. With the use of the organometallic iridium complex of one embodiment of the present invention, which has high emission efficiency and high reliability, a highly efficient and long-lifetime light-emitting element can be provided.

The structure described in this embodiment can be used in appropriate combination with the structure described in any of the other embodiments.

Embodiment 3

In this embodiment, as one embodiment of the present invention, a light-emitting element in which two or more kinds of organic compounds as well as an organometallic iridium complex are used for a light-emitting layer is described.

Figure 2:
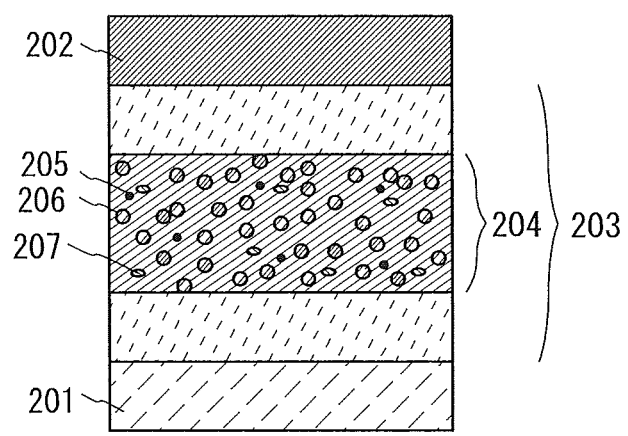
FIG. 2 illustrates a structure of a light-emitting element.

A light-emitting element described in this embodiment includes an EL layer 203 between a pair of electrodes (an anode 201 and a cathode 202) as illustrated in FIG. 2. Note that the EL layer 203 includes at least a light-emitting layer 204 and may include a hole-injection layer, a hole-transport layer, an electron-transport layer, an electron-injection layer, and the like. Note that for the hole-injection layer, the hole-transport layer, the electron-transport layer, and the electron-injection layer, the substances described in Embodiment 2 can be used.

The light-emitting layer 204 described in this embodiment contains a phosphorescent compound 205 using the organometallic iridium complex described in Embodiment 1, a first organic compound 206, and a second organic compound 207. Note that the phosphorescent compound 205 is a guest material in the light-emitting layer 204. Moreover, one of the first organic compound 206 and the second organic compound 207, the content of which is higher than that of the other in the light-emitting layer 204, is a host material in the light-emitting layer 204.

When the light-emitting layer 204 has the structure in which the guest material is dispersed in the host material, crystallization of the light-emitting layer can be suppressed. Further, it is possible to suppress concentration quenching due to high concentration of the guest material, and thus the light-emitting element can have higher emission efficiency.

Note that it is preferable that a triplet excitation energy level ($T_1$ level) of each of the first organic compound 206 and the second organic compound 207 be higher than that of the phosphorescent compound 205. The reason for this is that, when the $T_1$ level of the first organic compound 206 (or the second organic compound 207) is lower than that of the phosphorescent compound 205, the triplet excitation energy of the phosphorescent compound 205, which is to contribute to light emission, is quenched by the first organic compound 206 (or the second organic compound 207) and accordingly the emission efficiency decreases.

Here, for improvement in efficiency of energy transfer from a host material to a guest material, Förster mechanism (dipole-dipole interaction) and Dexter mechanism (electron exchange interaction), which are known as mechanisms of energy transfer between molecules, are considered. According to the mechanisms, it is preferable that an emission spectrum of a host material (a fluorescence spectrum in energy transfer from a singlet excited state, and a phosphorescence spectrum in energy transfer from a triplet excited state) largely overlap with an absorption spectrum of a guest material (specifically, a spectrum in an absorption band on the longest wavelength (lowest energy) side). However, in general, it is difficult to obtain an overlap between a fluorescence spectrum of a host material and an absorption spectrum in an absorption band on the longest wavelength (lowest energy) side of a guest material. The reason for this is as follows: if the fluorescence spectrum of the host material overlaps with the absorption spectrum in the absorption band on the longest wavelength (lowest energy) side of the guest material, since a phosphorescence spectrum of the host material is located on a longer wavelength (lower energy) side than the fluorescence spectrum, the $T_1$ level of the host material becomes lower than the $T_1$ level of the phosphorescent compound and the above-described problem of quenching occurs; yet, when the host material is designed in such a manner that the $T_1$ level of the host material is higher than the $T_1$ level of the phosphorescent compound in order to avoid the problem of quenching, the fluorescence spectrum of the host material is shifted to the shorter wavelength (higher energy) side, and thus the fluorescence spectrum does not have any overlap with the absorption spectrum in the absorption band on the longest wavelength (lowest energy) side of the guest material. For that reason, in general, it is difficult to obtain an overlap between a fluorescence spectrum of a host material and an absorption spectrum in an absorption band on the longest wavelength (lowest energy) side of a guest material so as to maximize energy transfer from a singlet excited state of a host material.

Thus, in this embodiment, a combination of the first organic compound 206 and the second organic compound 207 preferably forms an excited complex (also referred to as exciplex). In that case, the first organic compound 206 and the second organic compound 207 form an exciplex at the time of recombination of carriers (electrons and holes) in the light-emitting layer 204. Thus, in the light-emitting layer 204, a fluorescence spectrum of the first organic compound 206 and that of the second organic compound 207 are converted into an emission spectrum of the exciplex which is located on a longer wavelength side. Moreover, when the first organic compound 206 and the second organic compound 207 are selected in such a manner that the emission spectrum of the exciplex largely overlaps with the absorption spectrum of the guest material, energy transfer from a singlet excited state can be maximized. Note that also in the case of a triplet excited state, energy transfer from the exciplex, not the host material, is presumed to occur.

For the phosphorescent compound 205, the organometallic iridium complex described in Embodiment 1 is used. Although the combination of the first organic compound 206 and the second organic compound 207 can be determined such that an exciplex is formed, a combination of a compound which is likely to accept electrons (a compound having an electron-trapping property) and a compound which is likely to accept holes (a compound having a hole-trapping property) is preferably employed.

As a compound which is likely to accept electrons, for example, 2-[3-(dibenzothiophen-4-yl)phenyl]dibenzo[f,h]quinoxaline (abbreviation: 2mDBTPDBq-II), 2-[4-(3,6-diphenyl-9H-carbazol-9-yl)phenyl]dibenzo[f,h]quinoxaline (abbreviation: 2CzPDBq-III), 7-[3-(dibenzothiophen-4-yl)phenyl]dibenzo[f,h]quinoxaline (abbreviation: 7mDBTPDBq-II), and 6-[3-(dibenzothiophen-4-yl)phenyl]dibenzo[f,h]quinoxaline (abbreviation: 6mDBTPDBq-II).

As a compound which is likely to accept holes, for example, 4-phenyl-4'-(9-phenyl-9H-carbazol-3-yl)triphenylamine (abbreviation: PCBA1BP), 3-[N-(1-naphthyl)-N-(9-phenylcarbazol-3-yl)amino]-9-phenylcarbazole (abbreviation: PCzPCN1), 4,4',4''-tris[N-(1-naphthyl)-N-phenylamino]triphenylamine (abbreviation: 1'-TNATA), 2,7-bis[N-(4-diphenylaminophenyl)-N-phenylamino]-spiro-9,9'-bifluorene (abbreviation: DPA2SF), N,N'-bis(9-phenylcarbazol-3-yl)-N,N'-diphenylbenzene-1,3-diamine (abbreviation: PCA2B), N-(9,9-dimethyl-2-N',N'-diphenylamino-9H-fluoren-7-yl)diphenylamine (abbreviation: DPNF), N,N',N''-triphenyl-N,N',N''-tris(9-phenylcarbazol-3-yl)benzene-1,3,5-triamine (abbreviation: PCA3B), 2-[N-(9-phenylcarbazol-3-yl)-N-phenylamino]spiro-9,9'-bifluorene (abbreviation: PCASF), 2-[N-(4-diphenylaminophenyl)-N-phenylamino]spiro-9,9'-bifluorene (abbreviation: DPASF), N,N'-bis-[4-(carbazol-9-yl)phenyl]-N,N-diphenyl-9,9-dimethylfluorene-2,7-diamine (abbreviation: YGA2F), 4,4'-bis[N-(3-methylphenyl)-N-phenylamino]biphenyl (abbreviation: TPD), 4,4'-bis[N-(4-diphenylaminophenyl)-N-phenylamino]biphenyl (abbreviation: DPAB), N-(9,9-dimethyl-9H-fluoren-2-yl)-N-{9,9-dimethyl-2-[N'-phenyl-N'-(9,9-dimethyl-9H-flouren-2-yl)amino]-9H-fluoren-7-yl}phenylamine (abbreviation: DFLADFL), 3-[N-(9-phenylcarbazol-3-yl)-N-phenylamino]-9-phenylcarbazole (abbreviation: PCzPCA1), 3-[N-(4-diphenylaminophenyl)-N-phenylamino]-9-phenylcarbazole (abbreviation: PCzDPA1), 3,6-bis[N-(4-diphenylamimophenyl)-N-phenylamino]-9-phenylcarbazole (abbreviation: PCzDPA2), 4,4'-bis(N-{4-[N'-(3-methylphenyl)-N'-phenylamino]phenyl}-N-phenylamino)biphenyl (abbreviation: DNTPD), 3,6-bis[N-(4-diphenylaminophenyl)-N-(1-naphthyl)amino]-9-phenylcarbazole (abbreviation: PCzTPN2), and 3,6-bis[N-(9-phenylcarbazol-3-yl)-N-phenylamino]-9-phenylcarbazole (abbreviation: PCzPCA2).

As for the above-described first and second organic compounds 206 and 207, the present invention is not limited to the above examples. The combination is determined so that an exciplex can be formed, the emission spectrum of the exciplex overlaps with the absorption spectrum of the phosphorescent compound 205, and the peak of the emission spectrum of the exciplex has a longer wavelength than the peak of the absorption spectrum of the phosphorescent compound 205.

Note that in the case where a compound which is likely to accept electrons and a compound which is likely to accept holes are used for the first organic compound 206 and the second organic compound 207, carrier balance can be controlled by the mixture ratio of the compounds. Specifically, the ratio of the first organic compound to the second organic compound is preferably 1:9 to 9:1.

In the light-emitting element described in this embodiment, energy transfer efficiency can be improved owing to energy transfer utilizing an overlap between an emission spectrum of an exciplex and an absorption spectrum of a phosphorescent compound; accordingly, it is possible to achieve high external quantum efficiency of the light-emitting element.

Note that in another structure of one embodiment of the present invention, the light-emitting layer 204 can be formed using a host molecule having a hole-trapping property and a host molecule having an electron-trapping property as the two kinds of organic compounds (the first organic compound 206 and the second organic compound 207) other than the phosphorescent compound 205 (guest material) so that a phenomenon (guest coupled with complementary hosts: GCCH) occurs in which holes and electrons are introduced to guest molecules existing in the two kinds of host molecules and the guest molecules are brought into an excited state.

At this time, the host molecule having a hole-trapping property and the host molecule having an electron-trapping property can be respectively selected from the above-described compounds which are likely to accept holes and the above-described compounds which are likely to accept electrons.

The structure of the light-emitting element described in this embodiment is an example. The light-emitting element of one embodiment of the present invention can have a microcavity structure in addition to the structure.

The structure of the light-emitting layer described in this embodiment can be used for the layer emitting phosphorescence among light-emitting layers included in the stacked structure illustrated in FIG. 1B in Embodiment 2.

The structure described in this embodiment can be used in appropriate combination with the structure described in any of the other embodiments.

Embodiment 4

Described in this embodiment is a light-emitting element (hereinafter, a tandem light-emitting element) which has a structure in which a charge-generation layer is provided between a plurality of EL layers and the organometallic iridium complex is used as an EL material in the EL layers.

Figure 7A:
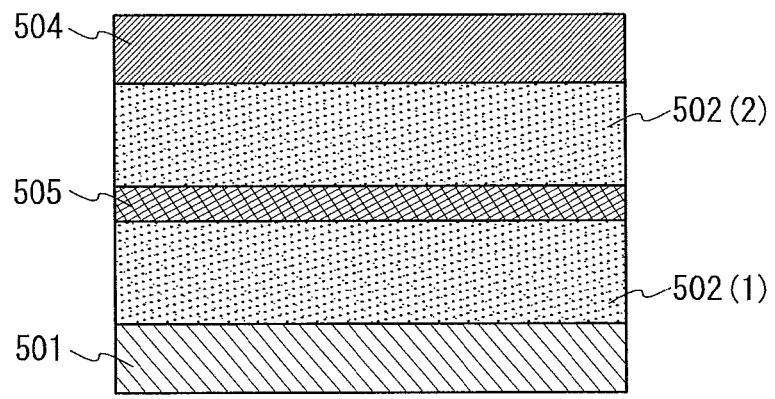
FIGS. 7A and 7B illustrate structures of light-emitting elements.

A light-emitting element described in this embodiment is a tandem light-emitting element including a plurality of EL layers (a first EL layer 502(1) and a second EL layer 502(2)) between a pair of electrodes (a first electrode 501 and a second electrode 504), as illustrated in FIG. 7A.

In this embodiment, the first electrode 501 functions as an anode, and the second electrode 504 functions as a cathode. Note that the first electrode 501 and the second electrode 504 can have structures similar to those described in Embodiment 2. In addition, either or both of the EL layers (the first EL layer 502(1) and the second EL layer 502(2)) may have structures similar to those described in Embodiment 2. In other words, the structures of the first EL layer 502(1) and the second EL layer 502(2) may be the same or different from each other and can be similar to those of the EL layers described in Embodiment 2.

In addition, a charge-generation layer 505 is provided between the plurality of EL layers (the first EL layer 502(1) and the second EL layer 502(2)). The charge-generation layer 505 has a function of injecting electrons into one of the EL layers and injecting holes into the other of the EL layers when voltage is applied between the first electrode 501 and the second electrode 504. In this embodiment, when voltage is applied such that the potential of the first electrode 501 is higher than that of the second electrode 504, the charge-generation layer 505 injects electrons into the first EL layer 502(1) and injects holes into the second EL layer 502(2).

Note that in terms of light extraction efficiency, the charge-generation layer 505 preferably has a property of transmitting visible light (specifically, the charge-generation layer 505 has a visible light transmittance of 40% or more). The charge-generation layer 505 functions even when it has lower conductivity than the first electrode 501 or the second electrode 504.

The charge-generation layer 505 may have either a structure in which an electron acceptor (acceptor) is added to an organic compound having a high hole-transport property or a structure in which an electron donor (donor) is added to an organic compound having a high electron-transport property. Alternatively, both of these structures may be stacked.

In the case of the structure in which an electron acceptor is added to an organic compound having a high hole-transport property, as the organic compound having a high hole-transport property, for example, an aromatic amine compound such as NPB, TPD, TDATA, MTDATA, or BSPB, or the like can be used. The substances listed here are mainly ones that have a hole mobility of $1\times10^{-6}$ cm$^2$/Vs or higher. Note that any organic compound other than the compounds listed here may be used as long as the hole-transport property is higher than the electron-transport property.

As the electron acceptor, 7,7,8,8-tetracyano-2,3,5,6-tetrafluoroquinodimethane (abbreviation: F$_4$-TCNQ), chloranil, and the like can be given. Oxides of metals belonging to Groups 4 to 8 of the periodic table can also be given. Specifically, vanadium oxide, niobium oxide, tantalum oxide, chromium oxide, molybdenum oxide, tungsten oxide, manganese oxide, and rhenium oxide are preferable because of their high electron-accepting properties. Among these, molybdenum oxide is especially preferable because it is stable in the air, has a low hygroscopic property, and is easy to handle.

In the case of the structure in which an electron donor is added to an organic compound having a high electron-transport property, as the organic compound having a high electron-transport property, for example, a metal complex having a quinoline skeleton or a benzoquinoline skeleton, such as Alq, Almq$_3$, BeBq$_2$, or BAlq, or the like can be used. Alternatively, a metal complex having an oxazole-based ligand or a thiazole-based ligand, such as Zn(BOX)$_2$ or Zn(BTZ)$_2$ can be used. Alternatively, in addition to such a metal complex, PBD, OXD-7, TAZ, Bphen, BCP, or the like can be used. The substances listed here are mainly ones that have an electron mobility of $1\times10^{-6}$ cm$^2$/Vs or higher. Note that any organic compound other than the compounds listed here may be used as long as the electron-transport property is higher than the hole-transport property.

As the electron donor, it is possible to use an alkali metal, an alkaline earth metal, a rare earth metal, metals belonging to Groups 2 and 13 of the periodic table, or an oxide or carbonate thereof. Specifically, lithium (Li), cesium (Cs), magnesium (Mg), calcium (Ca), ytterbium (Yb), indium (In), lithium oxide, cesium carbonate, or the like is preferably used. Alternatively, an organic compound such as tetrathianaphthacene may be used as the electron donor.

Note that forming the charge-generation layer 505 by using any of the above materials can suppress a drive voltage increase caused by the stack of the EL layers.

Figure 7B:
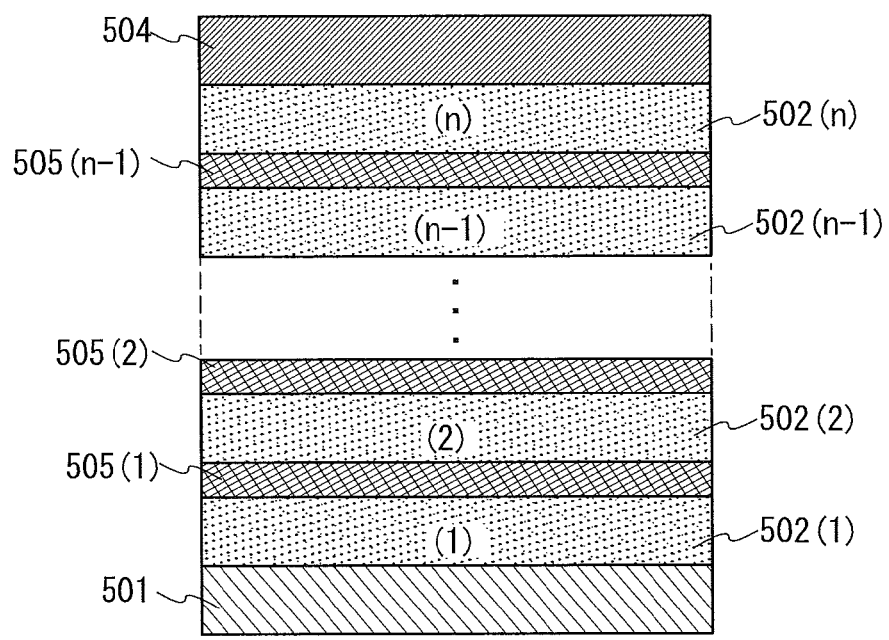

Although the light-emitting element including two EL layers is described in this embodiment, the present invention can be similarly applied to a light-emitting element in which n EL layers (502(1) to 502(n)) (n is three or more) are stacked as illustrated in FIG. 7B. In the case where a plurality of EL layers are included between a pair of electrodes as in the light-emitting element according to this embodiment, by providing charge-generation layers (505(1) to 505(n-1)) between the EL layers, light emission in a high luminance region can be obtained with current density kept low. Since the current density can be kept low, the element can have a long lifetime. When the light-emitting element is applied to light-emitting devices, electronic appliances, and lighting devices each having a large light-emitting area, voltage drop due to resistance of an electrode material can be reduced, which results in uniform light emission in a large area.

When the EL layers have different emission colors, a desired emission color can be obtained from the whole light-emitting element. For example, in a light-emitting element having two EL layers, when an emission color of the first EL layer and an emission color of the second EL layer are complementary colors, the light-emitting element can emit white light as a whole. Note that "complementary colors" refer to colors that can produce an achromatic color when mixed. In other words, emission of white light can be obtained by mixture of light emitted from substances whose emission colors are complementary colors. Specifically, a combination in which blue light emission is obtained from the first EL layer and yellow light emission or orange light emission is obtained from the second EL layer is given as an example. In that case, it is not necessary that both of blue light emission and yellow (or orange) light emission are fluorescence, and the both are not necessarily phosphorescence. For example, a combination in which blue light emission is fluorescence and yellow (or orange) light emission is phosphorescence or a combination in which blue light emission is phosphorescence and yellow (or orange) light emission is fluorescence may be employed. Moreover, a stacked structure suitable for adjustment of an optical path length of the light-emitting element (e.g., a structure in which the first light-emitting layer exhibits yellow light emission and the second light-emitting layer exhibits blue light emission) is preferably employed, in which case the element characteristics can be further improved.

The same can be applied to a light-emitting element having three EL layers. For example, the light-emitting element as a whole can provide white light emission when the emission color of the first EL layer is red, the emission color of the second EL layer is green, and the emission color of the third EL layer is blue.

Note that the structure described in this embodiment can be combined as appropriate with any of the structures described in the other embodiments.

Embodiment 5

In this embodiment, one embodiment of a light-emitting device in which the light-emitting element described in Embodiment 2 or 3 is combined with a coloring layer (e.g., a color filter) is described. In this embodiment, a structure of a pixel portion of the light-emitting device is described with reference to FIG. 8.

Figure 8:
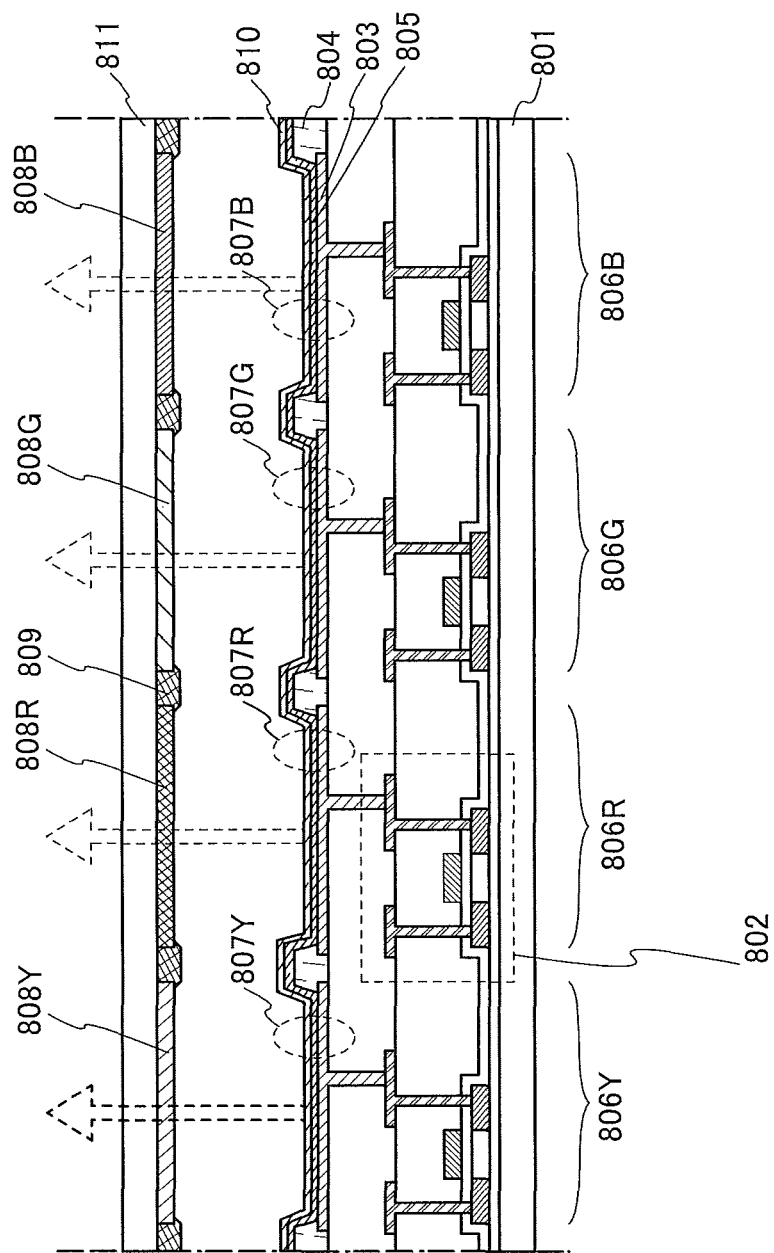
FIG. 8 illustrates a structure of a pixel portion of a light-emitting device.

In FIG. 8, a plurality of FETs 802 is formed over a substrate 801. Each of the FETs 802 is electrically connected to a light-emitting element (807R, 807G, 807B, or 807Y). Specifically, each of the FETs 802 is electrically connected to a first electrode 803 that is a pixel electrode of a light-emitting element. A partition wall 804 is provided to cover edge portions of adjacent first electrodes 803.

Note that the first electrode 803 in this embodiment has a function of a reflective electrode. An EL layer 805 is formed over the first electrode 803, and a second electrode 810 is formed over the EL layer 805. The EL layer 805 includes a plurality of light-emitting layers each emitting monochromatic light. The second electrode 810 has a function of a semi-transmissive and semi-reflective electrode.

The light-emitting elements (807R, 807G, 807B, and 807Y) emit light of different colors. Specifically, the light-emitting element 807R is optically adjusted to emit red light, and in a region indicated by 806R, red light is emitted through a coloring layer 808R in the direction indicated by an arrow. The light-emitting element 807G is optically adjusted to emit green light, and in a region indicated by 806G, green light is emitted through a coloring layer 808G in the direction indicated by an arrow. The light-emitting element 807B is optically adjusted to emit blue light, and in a region indicated by 806B, blue light is emitted through a coloring layer 808B in the direction indicated by an arrow. The light-emitting element 807Y is optically adjusted to emit yellow light, and in a region indicated by 806Y, yellow light may be emitted through a coloring layer 808Y in the direction indicated by an arrow.

As illustrated in FIG. 8, each of the coloring layers 808R, 808G, 808B, and 808Y is provided on a transparent sealing substrate 811 that is provided above the substrate 801 over which the light emitting elements 807R, 807G, 807B, and 807Y are formed. Note that the coloring layers 808R, 808G, 808B, and 808Y are provided in positions overlapping with the corresponding light-emitting elements 807R, 807G, 807B, and 807Y which exhibit different emission colors.

A black layer (black matrix) 809 may be provided to cover edge portions of adjacent coloring layers (808R, 808G, 808B, and 808Y). Note that the coloring layers 808R, 808G, 808B, and 808Y and the black layer 809 may be covered with an overcoat layer that is formed using a transparent material.

The above-described light-emitting device has a structure in which light is extracted from the sealing substrate 811 side (a top emission structure), but may have a structure in which light is extracted from the substrate 801 side where the FETs are formed (a bottom emission structure). Note that in the light-emitting device having a top emission structure described in this embodiment, a light-shielding substrate or a light-transmitting substrate can be used as the substrate 801, whereas in a light-emitting device having a bottom emission structure, a light-transmitting substrate needs to be used as the substrate 801.

Embodiment 6

Described in this embodiment is a light-emitting device that includes a light-emitting element in which the organometallic iridium complex of one embodiment of the present invention is used for an EL layer.

The light-emitting device may be either a passive matrix type light-emitting device or an active matrix type light-emitting device. Note that any of the light-emitting elements described in the other embodiments can be used for the light-emitting device described in this embodiment.

In this embodiment, an active matrix light-emitting device is described with reference to FIGS. 3A and 3B.

Figure 3A:
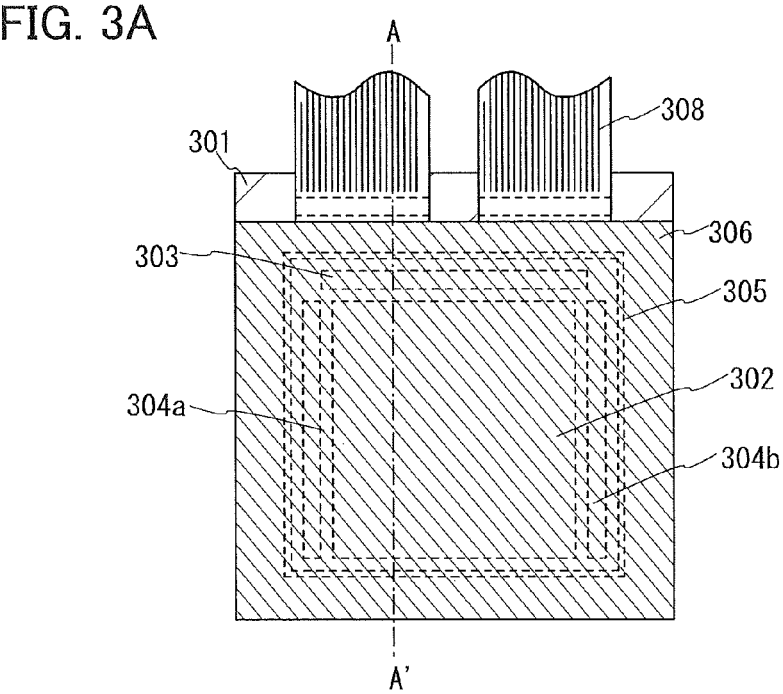
FIGS. 3A and 3B illustrate a light-emitting device.
Figure 3B:
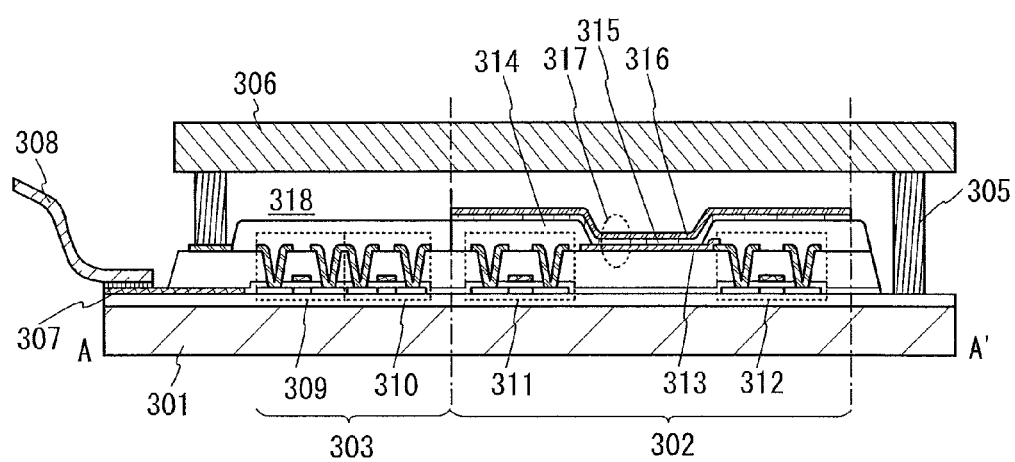

Note that FIG. 3A is a top view illustrating a light-emitting device and FIG. 3B is a cross-sectional view taken along the chain line A-A' in FIG. 3A. The active matrix light-emitting device according to this embodiment includes a pixel portion 302 provided over an element substrate 301, a driver circuit portion (a source line driver circuit) 303, and driver circuit portions 304*a* and 304*b*. The pixel portion 302, the driver circuit portion 303, and the driver circuit portions 304*a* and 304*b* are sealed between the element substrate 301 and a sealing substrate 306 with a sealant 305.

In addition, over the element substrate 301, a lead wiring 307 for connecting an external input terminal, through which a signal (e.g., a video signal, a clock signal, a start signal, a reset signal, or the like) or electric potential from the outside is transmitted to the driver circuit portion 303 and the driver circuit portions 304*a* and 304*b*, is provided.

Here, an example is described in which a flexible printed circuit (FPC) 308 is provided as the external input terminal. Although only the FPC is illustrated here, the FPC may be provided with a printed wiring board (PWB). The light-emitting device in this specification includes, in its category, not only the light-emitting device itself but also the light-emitting device provided with, the FPC or the PWB.

Next, a cross-sectional structure is described with reference to FIG. 3B. The driver circuit portion and the pixel portion are formed over the element substrate 301; the driver circuit portion 303 that is the source line driver circuit and the pixel portion 302 are illustrated here.

The driver circuit portion 303 is an example in which an FET 309 and an FET 310 are combined. Note that the driver circuit portion 303 may be formed with a circuit including transistors having the same conductivity type (either n-channel transistors or p-channel transistors) or a CMOS circuit including an n-channel transistor and a p-channel transistor. Although this embodiment shows a driver integrated type in which the driver circuit is formed over the substrate, the driver circuit is not necessarily formed over the substrate, and may be formed outside the substrate.

The pixel portion 302 includes a plurality of pixels each of which includes a switching FET 311, a current control FET 312, and a first electrode (anode) 313 which is electrically connected to a wiring (a source electrode or a drain electrode) of the current control FET 312. Although the pixel portion 302 includes two FETs, the switching FET 311 and the current control FET 312, in this embodiment, one embodiment of the present invention is not limited thereto. The pixel portion 302 may include, for example, three or more FETs and a capacitor in combination.

As the FETs 309, 310, 311, and 312, for example, a staggered transistor or an inverted staggered transistor can be used. For example, a Group 13 semiconductor (e.g., gallium), a Group 14 semiconductor (e.g., silicon), a compound semiconductor, an oxide semiconductor, or an organic semiconductor can be used. In addition, there is no particular limitation on the crystallinity of the semiconductor material, and an amorphous semiconductor or a crystalline semiconductor can be used. In particular, an oxide semiconductor is preferably used for the FETs 309, 310, 311, and 312. Examples of the oxide semiconductor include an In—Ga oxide and an In-M-Zn oxide (M is Al, Ga, Y, Zr, La, Ce, or Nd). For example, an oxide semiconductor that has an energy gap of 2 eV or more, preferably 2.5 eV or more, further preferably 3 eV or more is used for the FETs 309, 310, 311, and 312, so that the off-state current of the transistors can be reduced.

In addition, an insulator 314 is framed to cover end portions of the first electrode (anode) 313. In this embodiment, the insulator 314 is formed using a positive photosensitive acrylic resin. The first electrode 313 is used as an anode in this embodiment.

The insulator 314 preferably has a curved surface with curvature at an upper end portion or a lower end portion thereof. This enables the coverage with a film to be formed over the insulator 314 to be favorable. The insulator 314 can be formed using, for example, either a negative photosensitive resin or a positive photosensitive resin. The material of the insulator 314 is not limited to an organic compound and an inorganic compound such as silicon oxide, silicon oxynitride, or silicon nitride can also be used.

An EL layer 315 and a second electrode (cathode) 316 are stacked over the first electrode (anode) 313. In the EL layer 315, at least a light-emitting layer is provided. In the EL layer 315, a hole-injection layer, a hole-transport layer, an electron-transport layer, an electron-injection layer, a charge-generation layer, and the like can be provided as appropriate in addition to the light-emitting layer.

A light-emitting element 317 is formed of a stack of the first electrode (anode) 313, the EL layer 315, and the second electrode (cathode) 316. For the first electrode (anode) 313, the EL layer 315, and the second electrode (cathode) 316, any of the materials given in Embodiment 2 can be used. Although not illustrated, the second electrode (cathode) 316 is electrically connected to the FPC 308 which is an external input terminal.

Although the cross-sectional view in FIG. 3B illustrates only one light-emitting element 317, a plurality of light-emitting elements are arranged in a matrix in the pixel portion 302. Light-emitting elements that emit light of three kinds of colors (R, G, and B) are selectively formed in the pixel portion 302, whereby a light-emitting device capable of full color display can be obtained. In addition to the light-emitting elements that emit light of three kinds of colors (R, G, and B), for example, light-emitting elements that emit light of white (W), yellow (Y), magenta (M), cyan (C), and the like may be formed. For example, the light-emitting elements that emit light of a plurality of kinds of colors are used in combination with the light-emitting elements that emit light of three kinds of colors (R, G, and B), whereby effects such as an improvement in color purity and a reduction in power consumption can be obtained. Alternatively, the light-emitting device may be capable of full color display by combination with color filters. The light-emitting device may have improved emission efficiency and reduced power consumption by combination with quantum dots.

Furthermore, the sealing substrate 306 is attached to the element substrate 301 with the sealant 305, whereby a light-emitting element 317 is provided in a space 318 surrounded by the element substrate 301, the sealing substrate 306, and the sealant 305. Note that the space 318 may be filled with an inert gas (such as nitrogen and argon) or the sealant 305.

An epoxy-based resin or glass frit is preferably used for the sealant 305. The material preferably allows as little moisture and oxygen as possible to penetrate. As the sealing substrate 306, a glass substrate, a quartz substrate, or a plastic substrate formed of fiber-reinforced plastic (FRP), polyvinyl fluoride) (PVF), polyester, acrylic, or the like can be used. In the case where glass frit is used as the sealant, the element substrate 301 and the sealing substrate 306 are preferably glass substrates for high adhesion.

As described above, an active matrix light-emitting device can be obtained.

Note that the structure described in this embodiment can be combined as appropriate with any of the structures described in the other embodiments.

Embodiment 7

In this embodiment, examples of an electronic appliance manufactured using a light-emitting device which is one embodiment of the present invention are described with reference to FIGS. 4A to 4D and FIGS. 5A to 5C.

Examples of the electronic appliance including the light-emitting device are television devices (also referred to as TV or television receivers), monitors for computers and the like, cameras such as digital cameras and digital video cameras, digital photo frames, cellular phones (also referred to as portable telephone devices), portable game consoles, portable information terminals, audio playback devices, large game machines such as pachinko machines, and the like. Specific examples of the electronic appliances are illustrated in FIGS. 4A to 4D.

Figure 4A:
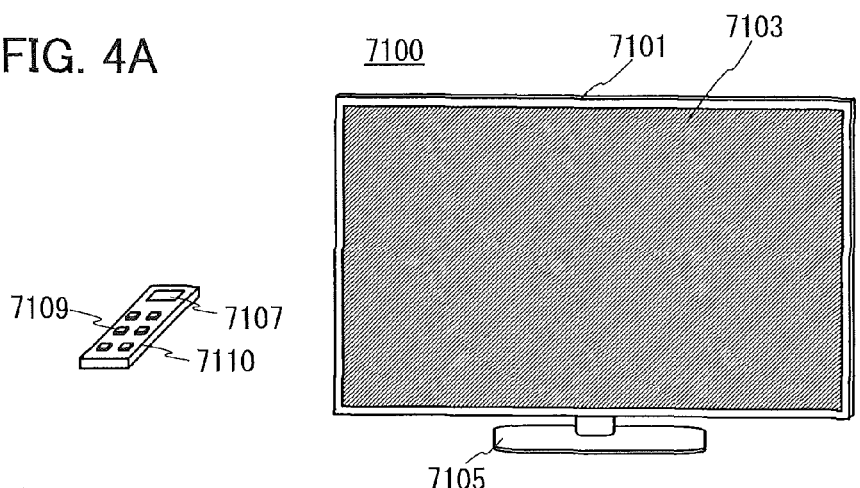
FIGS. 4A to 4D, 4D'1, and 4D'2 illustrate electronic devices.

FIG. 4A illustrates an example of a television device. In the television device 7100, a display portion 7103 is incorporated in a housing 7101. The display portion 7103 can display images and may be a touch panel (an input/output device) including a touch sensor (an input device). Note that the light-emitting device which is one embodiment of the present invention can be used for the display portion 7103. In addition, here, the housing 7101 is supported by a stand 7105.

The television device 7100 can be operated by an operation switch of the housing 7101 or a separate remote controller 7110. With operation keys 7109 of the remote controller 7110, channels and volume can be controlled and images displayed on the display portion 7103 can be controlled. Furthermore, the remote controller 7110 may be provided with a display portion 7107 for displaying data output from the remote controller 7110.

Note that the television device 7100 is provided with a receiver, a modem, and the like. With the use of the receiver, general television broadcasts can be received. Moreover, when the television device is connected to a communication network with or without wires via the modem, one-way (from a sender to a receiver) or two-way (between a sender and a receiver or between receivers) information communication can be performed.

Figure 4B:
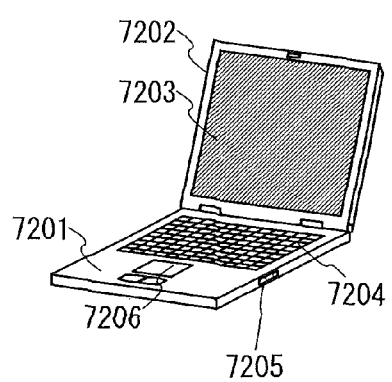

FIG. 4B illustrates a computer, which includes a main body 7201, a housing 7202, a display portion 7203, a keyboard 7204, an external connection port 7205, a pointing device 7206, and the like. Note that this computer can be manufactured using the light-emitting device which is one embodiment of the present invention for the display portion 7203. The display portion 7203 may be a touch panel (an input/output device) including a touch sensor (an input device).

Figure 4C:
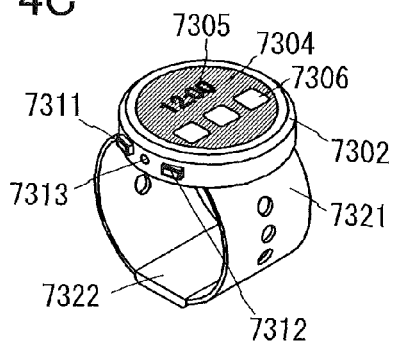

FIG. 4C illustrates a smart watch, which includes a housing 7302, a display panel 7304, operation buttons 7311 and 7312, a connection terminal 7313, a band 7321, a clasp 7322, and the like.

The display panel 7304 mounted in the housing 7302 serving as a bezel includes a non-rectangular display region. The display panel 7304 can display an icon 7305 indicating time, another icon 7306, and the like. The display panel 7304 may be a touch panel (an input/output device) including a touch sensor (an input device).

The smart watch illustrated in FIG. 4C can have a variety of functions, for example, a function of displaying a variety of information (e.g., a still image, a moving image, and a text image) on a display portion, a touch panel function, a function of displaying a calendar, date, time, and the like, a function of controlling processing with a variety of software (programs), a wireless communication function, a function of being connected to a variety of computer networks with a wireless communication function, a function of transmitting and receiving a variety of data with a wireless communication function, and a function of reading program or data stored in a recording medium and displaying the program or data on a display portion.

The housing 7302 can include a speaker, a sensor (a sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared rays), a microphone, and the like. Note that the smart watch can be manufactured using the light-emitting device for the display panel 7304.

Figure 4D:
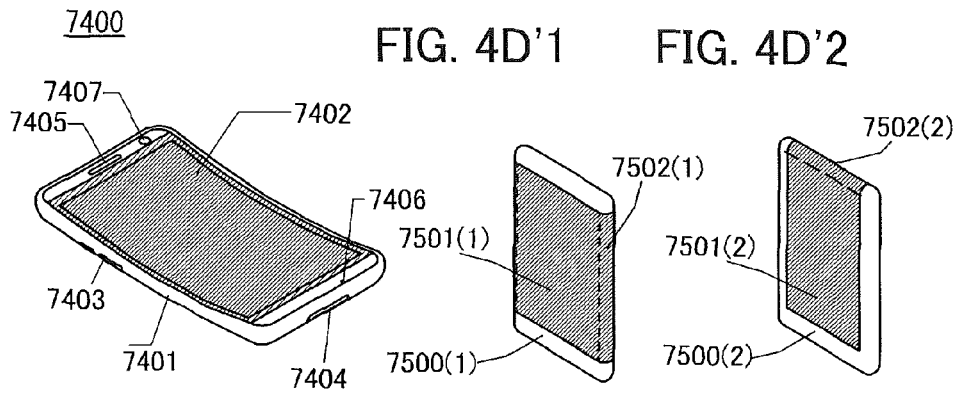

FIG. 4D illustrates an example of a cellular phone (e.g., smartphone). A cellular phone 7400 includes a housing 7401 provided with a display portion 7402, a microphone 7406, a speaker 7405, a camera 7407, an external connection portion 7404, an operation button 7403, and the like. In the case where a light-emitting device is manufactured by forming a light-emitting element of one embodiment of the present invention over a flexible substrate, the light-emitting element can be used for the display portion 7402 having a curved surface as illustrated in FIG. 4D.

When the display portion 7402 of the cellular phone 7400 illustrated in FIG. 4D is touched with a finger or the like, data can be input to the cellular phone 7400. In addition, operations such as making a call and composing an e-mail can be performed by touch on the display portion 7402 with a finger or the like.

There are mainly three screen modes of the display portion 7402. The first mode is a display mode mainly for displaying an image. The second mode is an input mode mainly for inputting data such as characters. The third mode is a display-and-input mode in which two modes of the display mode and the input mode are combined.

For example, in the case of making a call or creating e-mail, a character input mode mainly for inputting characters is selected for the display portion 7402 so that characters displayed on the screen can be input. In this case, it is preferable to display a keyboard or number buttons on almost the entire screen of the display portion 7402.

When a detection device such as a gyroscope or an acceleration sensor is provided inside the cellular phone 7400, display on the screen of the display portion 7402 can be automatically changed by determining the orientation of the cellular phone 7400 (whether the cellular phone is placed horizontally or vertically for a landscape mode or a portrait mode).

The screen modes are changed by touch on the display portion 7402 or operation with the button 7403 of the housing 7401. The screen modes can be switched depending on the kind of images displayed on the display portion 7402. For example, when a signal of an image displayed on the display portion is a signal of moving image data, the screen mode is switched to the display mode. When the signal is a signal of text data, the screen mode is switched to the input mode.

Moreover, in the input mode, if a signal detected by an optical sensor in the display portion 7402 is detected and the input by touch on the display portion 7402 is not performed for a certain period, the screen mode may be controlled so as to be changed from the input mode to the display mode.

The display portion 7402 may function as an image sensor. For example, an image of a palm print, a fingerprint, or the like is taken by touch on the display portion 7402 with the palm or the finger, whereby personal authentication can be performed. In addition, by providing a backlight or a sensing light source that emits near-infrared light in the display portion, an image of a finger vein, a palm vein, or the like can be taken.

The light-emitting device can be used for a cellular phone having a structure illustrated in FIG. 4D'1 or FIG. 4D'2, which is another structure of the cellular phone (e.g., smartphone).

Note that in the case of the structure illustrated in FIG. 4D'1 or FIG. 4D'2, text data, image data, or the like can be displayed on second screens 7502(1) and 7502(2) of housings 7500(1) and 7500(2) as well as first screens 7501(1) and 7501(2). Such a structure enables a user to easily see text data, image data, or the like displayed on the second screens 7502(1) and 7502(2) while the cellular phone is placed in user's breast pocket.

Figure 5A:
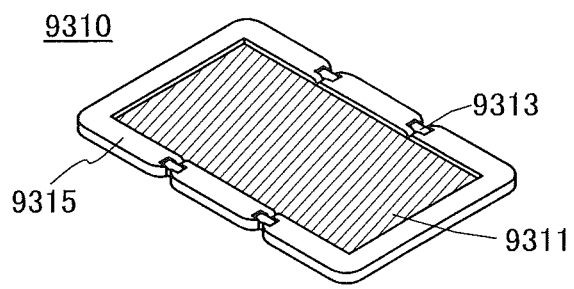
FIGS. 5A to 5C illustrate an electronic device.
Figure 5B:
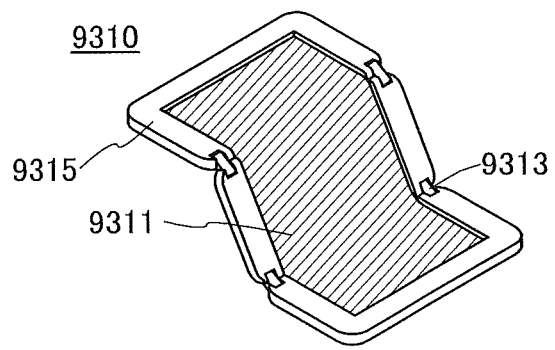
Figure 5C:
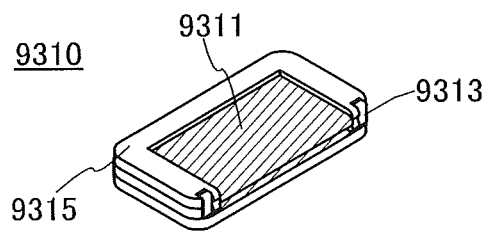

FIGS. 5A to 5C illustrate a foldable portable information terminal 9310. FIG. 5A illustrates the portable information terminal 9310 which is opened. FIG. 5B illustrates the portable information terminal 9310 which is being opened or being folded. FIG. 5C illustrates the portable information terminal 9310 that is folded. The portable information terminal 9310 is highly portable when folded. When the portable information terminal 9310 is opened, a seamless large display region is highly browsable.

A display panel 9311 is supported by three housings 9315 joined together by hinges 9313. Note that the display panel 9311 may be a touch panel (an input/output device) including a touch sensor (an input device). By bending the display panel 9311 at a connection portion between two housings 9315 with the use of the hinges 9313, the portable information terminal 9310 can be reversibly changed in shape from an opened state to a folded state. A light-emitting device of one embodiment of the present invention can be used for the display panel 9311. A display region 9312 is a display region that positioned at a side surface of the portable information terminal 9310 that is folded. On the display region 9312, information icons, file shortcuts of frequently used applications or programs, and the like can be displayed, and confirmation of information and start of application can be smoothly performed.

As described above, the electronic appliances can be obtained using the light-emitting device which is one embodiment of the present invention. Note that the light-emitting device can be used for electronic appliances in a variety of fields without being limited to the electronic appliances described in this embodiment.

Note that the structure described in this embodiment can be combined as appropriate with any of the structures described in the other embodiments.

Embodiment 8

In this embodiment, examples of a lighting device including the light-emitting device of one embodiment of the present invention are described with reference to FIG. 6.

Figure 6:
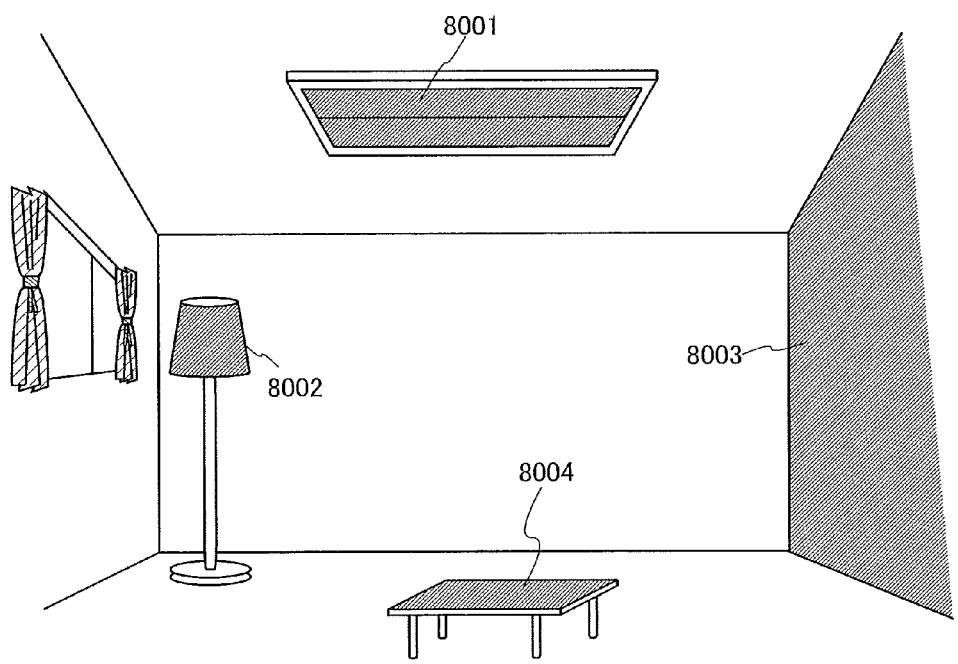
FIG. 6 illustrates lighting devices.

FIG. 6 illustrates an example in which the light-emitting device is used as an indoor lighting device 8001. Since the light-emitting device can have a large area, it can be used for a lighting device having a large area. In addition, with the use of a housing with a curved surface, a lighting device 8002 which includes the housing, a cover, or a support and in which a light-emitting region has a curved surface can also be obtained. A light-emitting element included in the light-emitting device described in this embodiment is in a thin film form, which allows the housing to be designed more freely. Thus, the lighting device can be elaborately designed in a variety of ways. In addition, a wall of the room may be provided with a large-sized lighting device 8003.

When the light-emitting device is used for a table by being used as a surface of a table, a lighting device 8004 that has a function as a table can be obtained. When the light-emitting device is used as part of other furniture, a lighting device that functions as the furniture can be obtained.

As described above, a variety of lighting devices that include the light-emitting device can be obtained. Note that these lighting devices are also embodiments of the present invention.

Note that the structure described in this embodiment can be combined as appropriate with any of the structures described in the other embodiments.

Example 1

Synthesis Example 1

In this example, a method for synthesizing bis[2-(5-phenyl-2-pyrimidinyl-κN)phenyl-κC](2,4-pentanedionato-κ$^2$O,O')iridium(III) (abbreviation: [Ir(5dppm2)$_2$(acac)]), which is an organometallic iridium complex of one embodiment of the present invention represented by Structural Formula (100) in Embodiment 1, is described. The structure of [Ir(5dppm2)$_2$(acac)] is shown below.

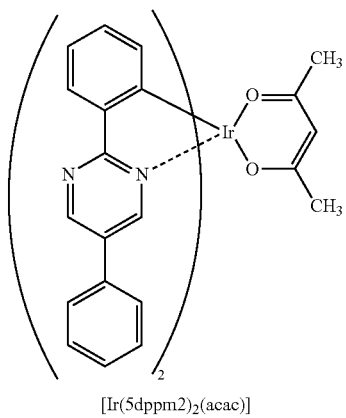

[Ir(5dppm2)$_2$(acac)]

Step 1: Synthesis of 2,5-diphenylpyrimidine

First, 5.0 g (26 mmol) of 5-bromo-2-chloropyrimidine, 7.0 g (57 mmol) of phenylboronic acid, 12 g (57 mmol) of tripotassium phosphate, 0.79 g (1.9 mmol) of 2-dicyclohexylphosphino-2',6'-dimethoxybiphenyl (S-Phos), and 250 mL of toluene were put in a 500-mL three-neck flask, and the atmosphere in the flask was replaced with nitrogen. To this mixture was added 174 mg (0.77 mmol) of palladium(II) acetate, and stirring was performed at 80° C. for 11 hours and at 100° C. for 8 hours. After a predetermined time, 319 mg (1.42 mmol) of palladium(II)acetate and 1.2 g (2.8 mmol) of 2-dicyclohexylphosphino-2',6'-dimethoxybiphenyl (S-Phos) were added to this mixture, and the mixture was heated and stirred at 100° C. for 8 hours. Water was added to the reaction mixture, and an aqueous layer of this mixture was subjected to extraction with toluene. The obtained solution of the extract and the organic layer were combined and washed with saturated brine, and anhydrous magnesium sulfate was added for drying. This mixture was subjected to gravity filtration, and the filtrate was concentrated to give a solid. This solid was dissolved in toluene, and the resulting solution was filtered through Celite, alumina, and Florisil stacked in this order on a piece of filter paper. The obtained filtrate was concentrated to give a solid. The solid was recrystallized with toluene. Thus, 2,5-diphenylpyrimidine (white solid) was obtained in a yield of 50%. A synthesis scheme of Step 1 is shown in (a-1).

(a-1)

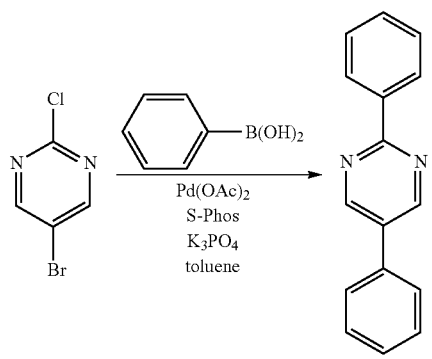

Step 2: Synthesis of di-μ-chloro-tetrakis[2-(5-phenyl-2-pyrimidinyl-κN)phenyl-κC]diiridium(III) (Abbreviation: [Ir(5dppm2)$_2$Cl]$_2$)

Next, 1.8 g (8.1 mmol) of the ligand H5dppm2, which was obtained through Step 1, 1.2 g (3.8 mmol) of iridium(III) chloride hydrate, 15 mL of 2-ethoxyethanol, and 5 mL of water were put in a 50-mL recovery flask, and the atmosphere in the flask was replaced with argon. This reaction container was heated by irradiation with microwaves under conditions of 100° C. and 100 W for 1 hour to cause a reaction. After a predetermined time, the reacted solution was concentrated to give a residue, and the residue was washed with ethanol, whereby a dinuclear complex [Ir(5dppm2)$_2$Cl]$_2$ (orange powder) was obtained in a yield of 97%. A synthesis scheme of Step 2 is shown in (a-2).

(a-2)

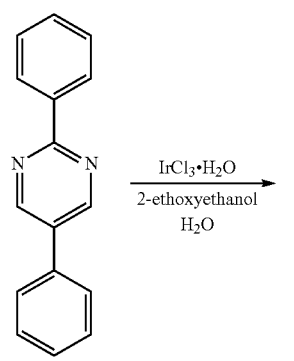

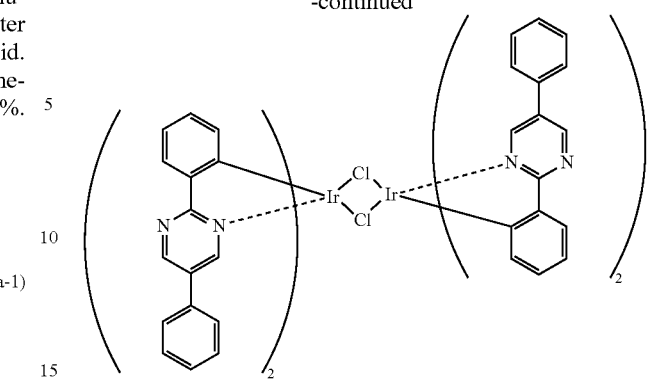

[Ir(5dppm2)$_2$Cl]$_2$

Step 3: Synthesis of bis[2-(5-phenyl-2-pyrimidinyl-κN)phenyl-κC](2,4-pentanedionato-κ$^2$O,O')iridium(III) (Abbreviation: [Ir(5dppm2)$_2$(acac)])

Next, 2.5 g (1.8 mmol) of the dinuclear complex [Ir(5dppm2)$_2$Cl]$_2$ obtained through Step 2, 1.9 g (18 mmol) of sodium carbonate, 0.55 g (5.5 mmol) of acetylacetone, and 40 mL of 2-ethoxyethanol were put in a 100-mL round-bottom flask, and the atmosphere in the flask was replaced with argon. This reaction container was irradiated with microwaves under conditions of 110° C. and 120 W for 1 hour to cause a reaction. After a predetermined time, water was added to the reacted mixture, and an aqueous layer of this mixture was subjected to extraction with dichloromethane. The obtained solution of the extract was washed with saturated brine, and anhydrate magnesium sulfate was added to the organic layer for drying. The obtained mixture was subjected to gravity filtration to give a filtrate. The obtained filtrate was concentrated to give a solid. The solid was dissolved in dichloromethane, and the resulting solution was filtered through alumina. The obtained filtrate was concentrated to give a residue, and the residue was recrystallized with a mixed solvent of dichloromethane and hexane. Thus, the organometallic complex of one embodiment of the present invention, [Ir(5dppm2)$_2$(acac)] (orange powder) was obtained in a yield of 30%. A synthesis scheme of Step 3 is shown in (a-3).

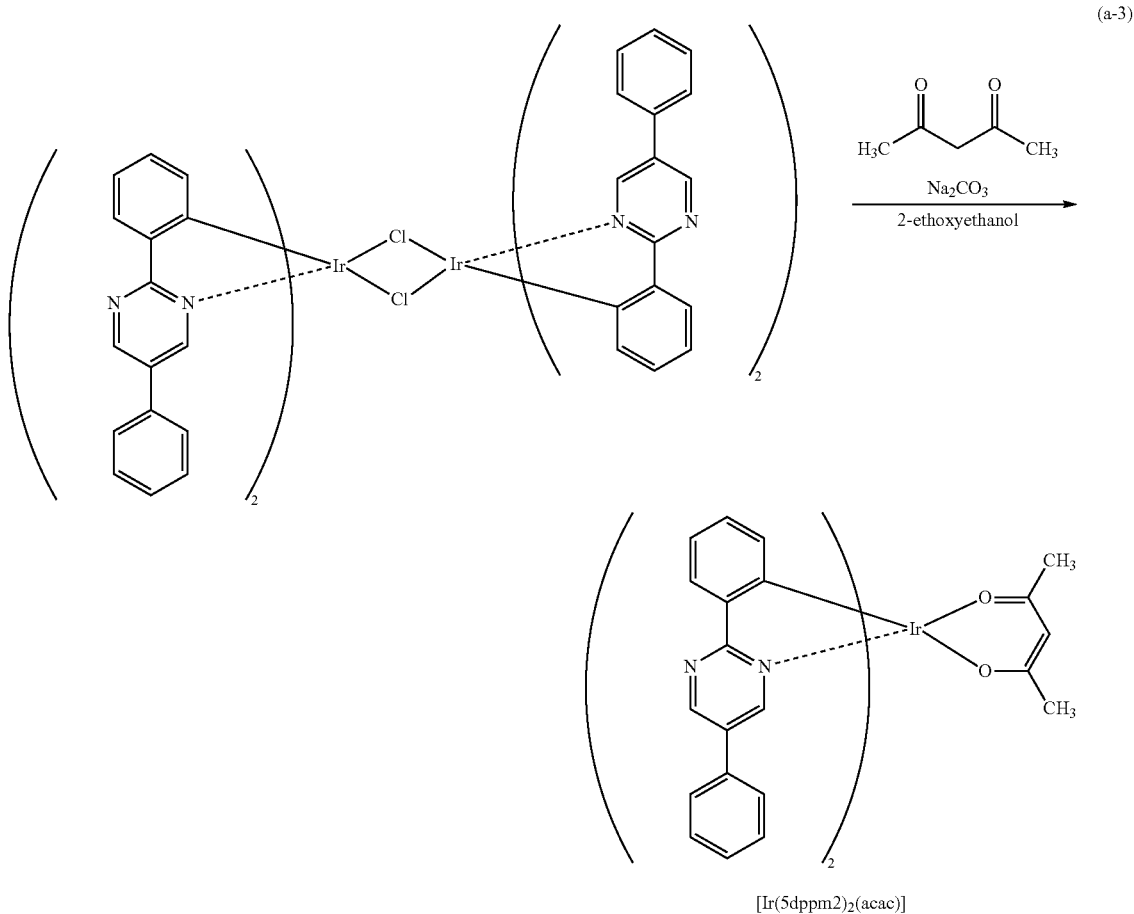

[Ir(5dppm2)₂(acac)]

Figure 9:
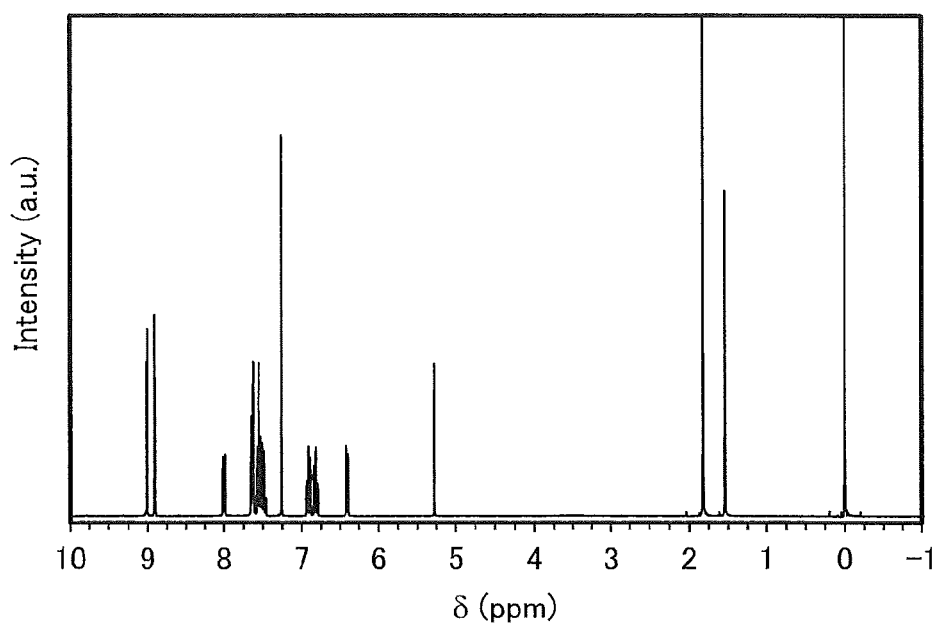
FIG. 9 is a $^1$H-NMR chart of an organometallic iridium complex represented by Structural Formula (100).

An analysis result by nuclear magnetic resonance (¹H-NMR) spectroscopy of the orange powder obtained in Step 3 is described below. FIG. 9 shows the ¹H-NMR chart. The result revealed that the organometallic iridium complex of one embodiment of the present invention [Ir(5dppm2)₂(acac)] represented by Structural Formula (100), was obtained in Synthesis Example 1.

¹H-NMR. δ (CDCl₃): 1.82 (s, 6H), 5.23 (s, 1H), 6.40 (d, 2H), 6.89 (t, 2H), 6.93 (t, 2H), 7.45-7.65 (m, 10H), 8.00 (dd, 2H), 8.90 (d, 2H), 9.01 (d, 2H).

Figure 10:
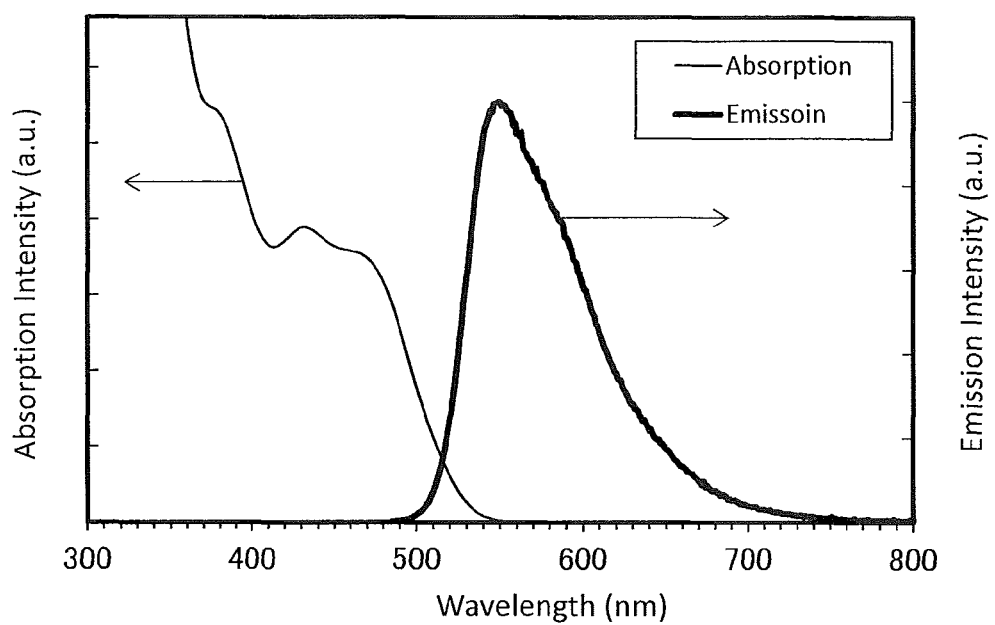
FIG. 10 shows an ultraviolet-visible absorption spectrum and an emission spectrum of an organometallic iridium complex represented by Structural Formula (100).

Next, an ultraviolet-visible absorption spectrum (hereinafter, simply referred to as an absorption spectrum) and an emission spectrum of [Ir(5dppm2)₂(acac)] in a dichloromethane solution were measured. The measurement of the absorption spectrum was conducted at room temperature, for which an ultraviolet-visible light spectrophotometer (V550 type manufactured by JASCO Corporation) was used and the dichloromethane solution (0.092 mmol/L) was put in a quartz cell. The measurement of the emission spectrum was conducted at room temperature, for which a fluorescence spectrophotometer (FS920, manufactured by Hamamatsu Photonics K.K.) was used and the degassed dichloromethane solution (0.092 mmol/L) was put in a quartz cell. FIG. 10 shows measurement results of the absorption spectrum and the emission spectrum. The horizontal axis represents wavelength and the vertical axes represent absorption intensity and emission intensity. In FIG. 10, two solid lines are shown; a thin line represents the absorption spectrum, and a thick line represents the emission spectrum. The absorption spectrum in FIG. 10 is a result obtained in such a way that the measured absorption spectrum of only dichloromethane that was in a quartz cell was subtracted from the measured absorption spectrum of the dichloromethane solution (0.092 mmol/L) that was in a quartz cell.

As shown in FIG. 10, [Ir(5dppm2)₂(acac)], the organometallic iridium complex of one embodiment of the present invention, has an emission peak at 549 nm, and yellow light emission was observed from the dichloromethane solution.

Example 2

Figure 11:
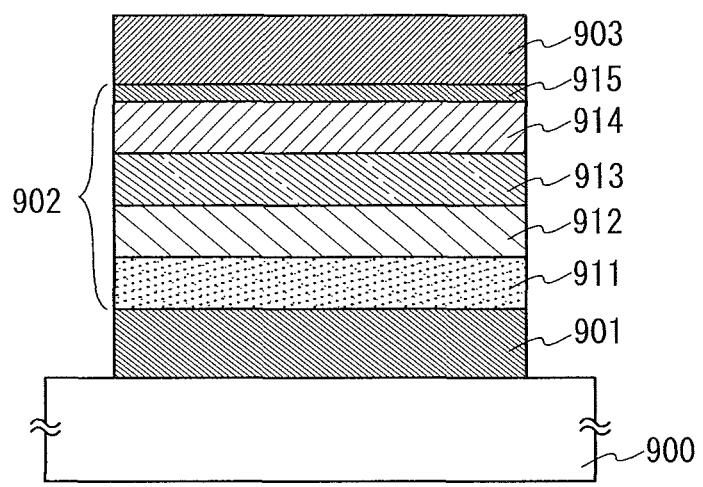
FIG. 11 illustrates a light-emitting element.

In this example, Light-emitting Element 1 and Comparative Light-emitting Element 2 were fabricated and emission spectra of these elements were measured. For a light-emitting layer of Light-emitting Element 1, [Ir(5dppm2)₂(acac)], which is the organometallic iridium complex of one embodiment of the present invention represented by Structural Formula (100), was used. For a light-emitting layer of Comparative Light-emitting Element 2, [Ir(ppm2-dmp)₂(acac)], which is an organometallic iridium complex, was used. Note that the fabrication of Light-emitting Element 1 and Comparative Light-emitting Element 2 is described with reference to FIG. 11. Chemical formulae of materials used in this example are shown below.

-continued
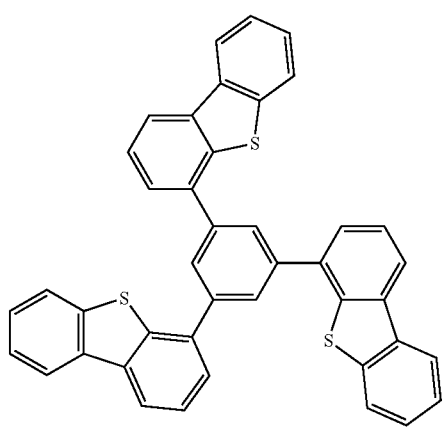
DBT3P-II
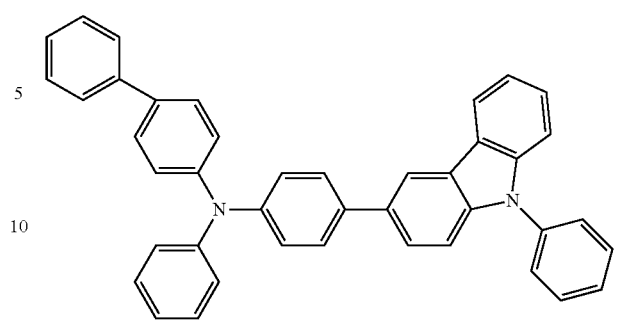
PCBA1BP
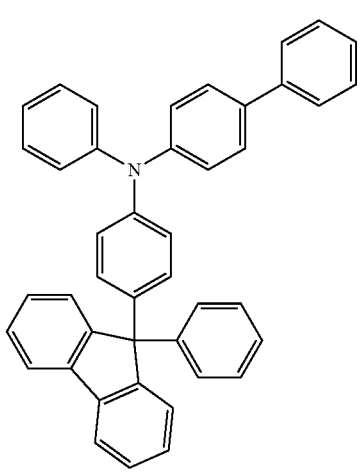
BPAFLP
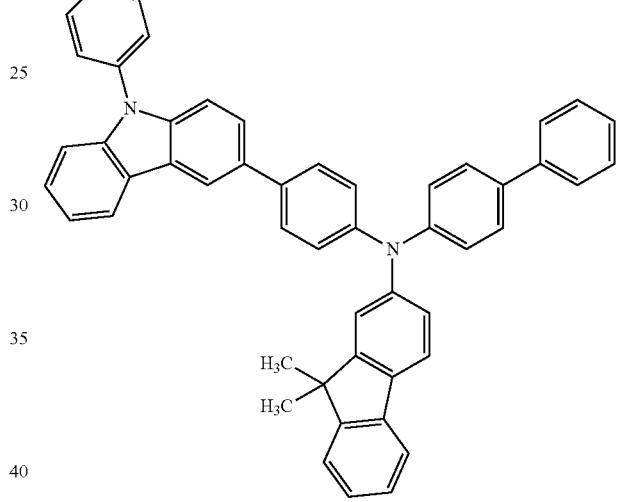
PCBBiF
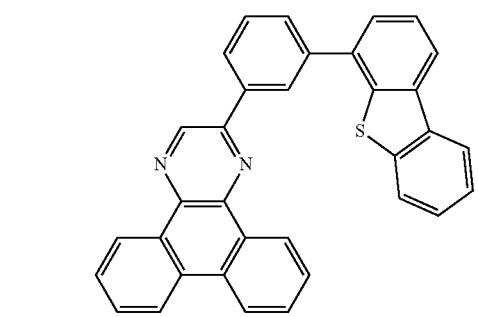
2mDBTPDBq-II
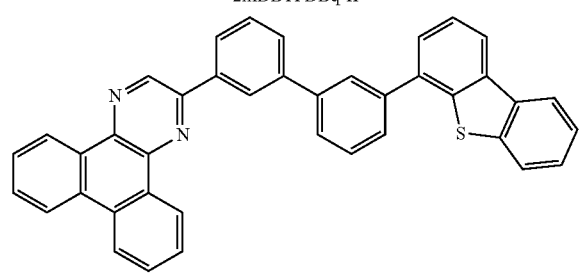
2mDBTBPDBq-II
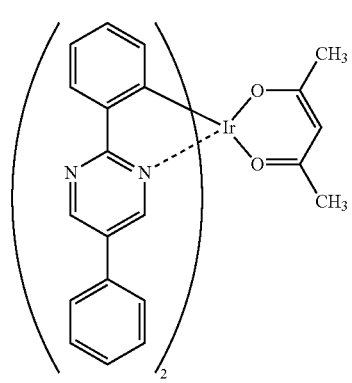
(100)
[Ir(5dppm2)$_2$(acac)]

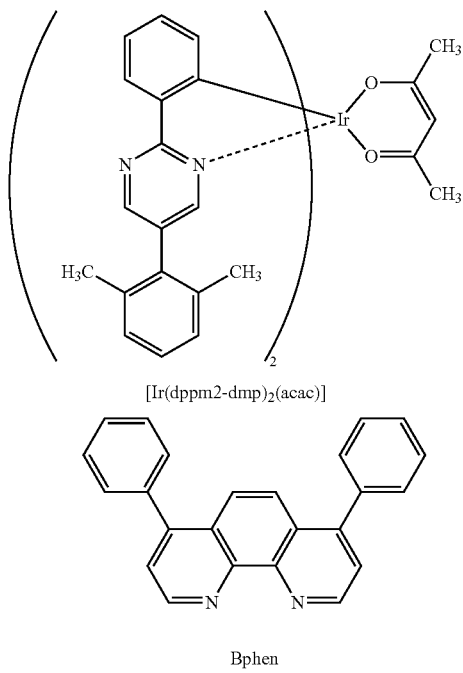

[Ir(dppm2-dmp)₂(acac)]

Bphen

<<Fabrication of Light-Emitting Element 1 and Comparative Light-Emitting Element 2>>

First, indium tin oxide containing silicon oxide (ITSO) was deposited over a glass substrate 900 by a sputtering method, whereby a first electrode 901 functioning as an anode was formed. Note that the thickness was set to 110 nm and the electrode area was set to 2 mm×2 mm.

Next, as pretreatment for fabricating Light-emitting Element 1 and Comparative Light-emitting Element 2 over the substrate 900, UV ozone treatment was performed for 370 seconds after washing of a surface of the substrate with water and baking that was performed at 200° C. for 1 hour.

After that, the substrate was transferred into a vacuum evaporation apparatus where the pressure had been reduced to approximately $10^{-4}$ Pa, and subjected to vacuum baking at 170° C. in a heating chamber of the vacuum evaporation apparatus for 30 minutes, and then the substrate 900 was cooled down for approximately 30 minutes.

Next, the substrate 900 was fixed to a holder provided in the vacuum evaporation apparatus so that a surface of the substrate over which the first electrode 901 was formed faced downward. In this example, a case is described in which a hole-injection layer 911, a hole-transport layer 912, a light-emitting layer 913, an electron-transport layer 914, and an electron-injection layer 915, which are included in an EL layer 902, are sequentially formed by a vacuum evaporation method.

After reducing the pressure in the vacuum evaporation apparatus to $10^{-4}$ Pa, 1,3,5-tri(dibenzothiophen-4-yl)benzene (abbreviation: DBT3P-II) and molybdenum(VI)oxide were deposited by co-evaporation so that the mass ratio of DBT3P-II to molybdenum oxide was 4:2, whereby the hole-injection layer 911 was formed over the first electrode 901. The thickness of the hole-injection layer 911 was set to 20 nm. Note that co-evaporation is an evaporation method in which a plurality of different substances are concurrently vaporized from different evaporation sources.

Next, 4-phenyl-4'-(9-phenylfluoren-9-yl)triphenylamine (abbreviation: BPAFLP) was deposited by evaporation to a thickness of 20 nm, whereby the hole-transport layer 912 was formed.

Next, the light-emitting layer 913 was formed over the hole-transport layer 912. The light-emitting layer 913 in Light-emitting Element 1 was formed by co-evaporation of 2-[3-(dibenzothiophen-4-yl)phenyl]dibenzo[f,h]quinoxaline (abbreviation: 2mDBTPDBq-II), 4-phenyl-4'-(9-phenyl-9H-carbazol-3-yl)triphenylamine (abbreviation: PCBA1BP), and bis[2-(5-phenyl-2-pyrimidinyl-κN)phenyl-κC](2,4-pentanedionato-κ²O,O')iridium(III) (abbreviation: [Ir(5dppm2)₂(acac)]) with a mass ratio of 2mDBTPDBq-II to PCBA1BP to [Ir(5dppm2)₂(acac)] being 0.8:0.2:0.025. The thickness of the light-emitting layer 913 was set to 40 nm.

The light-emitting layer 913 in Comparative Light-emitting Element 2 was formed by co-evaporation of 2-[3'-(dibenzothiophen-4-yl)biphenyl-3-yl]dibenzo[f,h]quinoxaline (abbreviation: 2mDBTBPDBq-II), N-(1,1'-biphenyl-4-yl)-N-[4-(9-phenyl-9H-carbazol-3-yl)phenyl]-9,9-dimethyl-9H-fluoren-2-amine (abbreviation: PCBBiF), and bis{2-[5-(2,6-dimethylphenyl)-2-pyrimidinyl-κN]phenyl-κC}(2,4-pentanedionato-κ²O,O')iridium(III) (abbreviation: [Ir(ppm2-dmp)₂(acac)]) with a mass ratio of 2mDBTBPDBq-II to PCBBiF to [Ir(ppm2-dmp)₂(acac)] being 0.8:0.2:0.025. The thickness of the light-emitting layer 913 was set to 40 nm.

Next, the electron-transport layer 914 in Light-emitting Element 1 was formed in such a manner that 2mDBTPDBq-II was deposited by evaporation over the light-emitting layer 913 to a thickness of 10 nm and then bathophenanthroline (abbreviation: Bphen) was deposited by evaporation to a thickness of 20 nm. The electron-transport layer 914 in Comparative Light-emitting Element 2 was formed in such a manner that 2mDBTBPDBq-II was deposited to a thickness of 10 nm and then Bphen was deposited to a thickness of 15 nm. Furthermore, the electron-injection layer 915 was found over the electron-transport layer 914 by evaporation of lithium fluoride to a thickness of 1 nm.

Finally, aluminum was deposited to a thickness of 200 nm over the electron-injection layer 915, whereby a second electrode 903 functioning as a cathode was formed. Through the above-described steps, Light-emitting Element 1 and Comparative Light-emitting Element 2 were fabricated. Note that in all the above evaporation steps, evaporation was performed by a resistance-heating method.

Table 1 shows element structures of Light-emitting Element 1 and Comparative Light-emitting Element 2 fabricated as described above.

TABLE 1

| | First electrode | Hole-injection layer | Hole-transport layer | Light-emitting layer | Electron-transport layer | | Electron-injection layer | Second electrode |
|---|---|---|---|---|---|---|---|---|
| Light-emitting Element 1 | ITSO (110 nm) | DBT3P-II:MoOx (4:2 20 nm) | BPAFLP (20 nm) | * | 2mDBTPD Bq II (10 nm) | Bphen (20 nm) | LiF (1 nm) | Al (200 nm) |

TABLE 1-continued

| | First electrode | Hole-injection layer | Hole-transport layer | Light-emitting layer | Electron-transport layer | | Electron-injection layer | Second electrode |
|---|---|---|---|---|---|---|---|---|
| Comparative Light-emitting Element 2 | ITSO (110 nm) | DBT3P-II:MoOx (4:2 20 nm) | BPAFLP (20 nm) | ** | 2mDBTBP DBq-II (10 nm) | Bphen (15 nm) | LiF (1 nm) | Al (200 nm) |

* 2mDBTPDBq-II:PCBA1BP:[Ir(5dppm2)$_2$(acac)] (0.8:0.2:0.025 (40 nm))
** 2mDBTBPDBq-II:PCBBiF:[Ir(ppm2-dmp)$_2$(acac)] (0.8:0.2:0.025 (40 nm))

Light-emitting Element 1 and Comparative Light-emitting Element 2 fabricated were sealed in a glove box under a nitrogen atmosphere so as not to be exposed to the air (specifically, a sealant was applied to surround the element, UV treatment was performed, and heat treatment was performed at 80° C. for 1 hour).

<<Operation Characteristics of Light-Emitting Element 1 and Comparative Light-Emitting Element 2>>

Operation characteristics of Light-emitting Element 1 and Comparative Light-emitting Element 2 fabricated were measured. Note that the measurements were carried out at room temperature (in an atmosphere kept at 25° C.).

Figure 12:
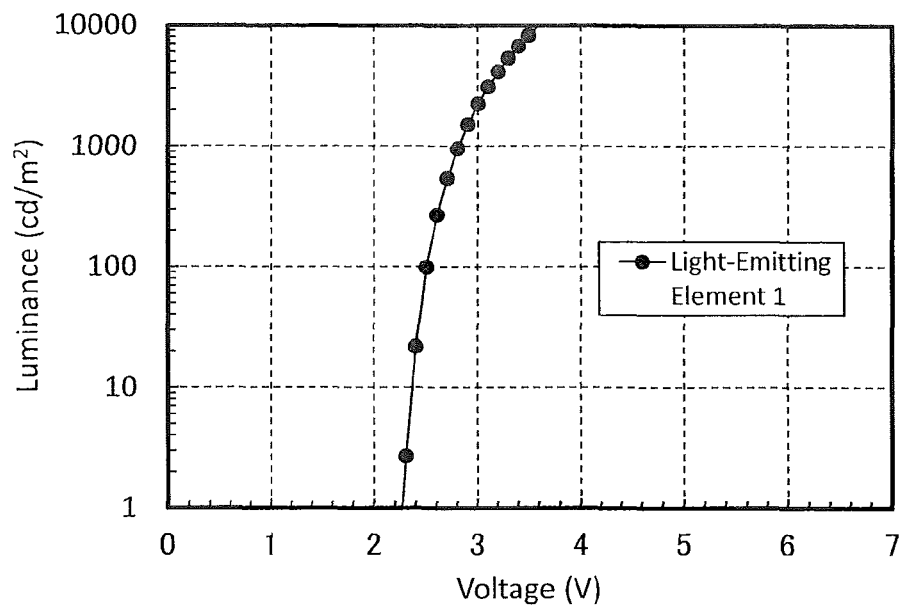
FIG. 12 shows voltage-luminance characteristics of Light-emitting Element 1.
Figure 13:
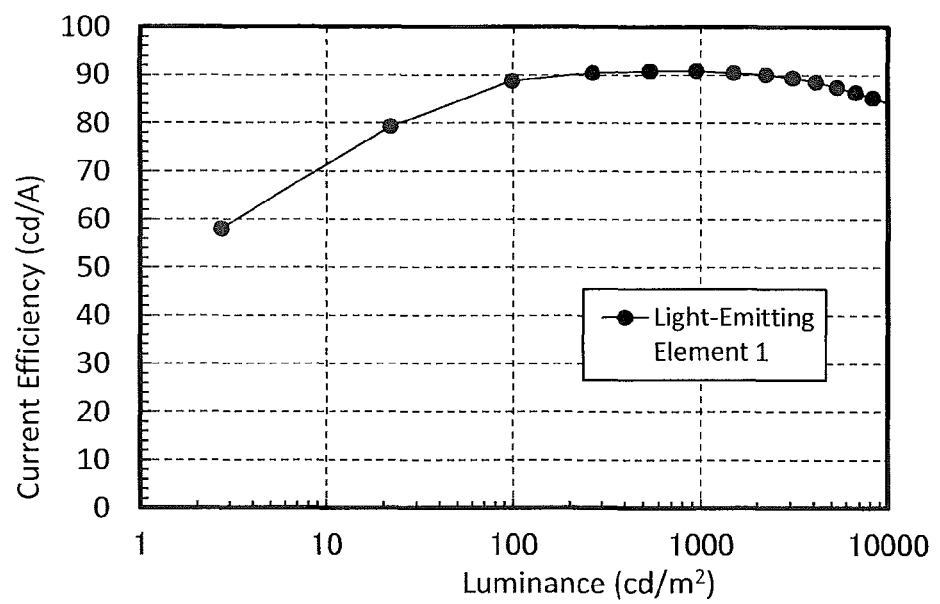
FIG. 13 shows luminance-current efficiency characteristics of Light-emitting Element 1.

First, FIG. 12 shows voltage-luminance characteristics of Light-emitting Element 1. In FIG. 12, the vertical axis represents luminance (cd/m$^2$) and the horizontal axis represents voltage (V). FIG. 13 shows luminance-current efficiency characteristics of Light-emitting Element 1. In FIG. 13, the vertical axis represents current efficiency (cd/A) and the horizontal axis represents luminance (cd/m$^2$). FIG. 13 reveals that Light-emitting Element 1 of one embodiment of the present invention has high efficiency.

Next, Table 2 shows initial values of main characteristics of Light-emitting Element 1 and Comparative Light-emitting Element 2 at a luminance of about 1000 cd/m$^2$.

TABLE 2

| | Voltage (V) | Current (mA) | Current density (mA/cm$^2$) | Chromaticity (x, y) | Luminance (cd/m$^2$) | Current Efficiency (cd/A) | Power efficiency (lm/W) | External quantum efficiency (%) |
|---|---|---|---|---|---|---|---|---|
| Light-emitting Element 1 | 2.8 | 0.041 | 1.0 | (0.45, 0.54) | 950 | 91 | 100 | 25 |
| Comparative Light-emitting Element 2 | 2.8 | 0.051 | 1.3 | (0.37, 0.61) | 1100 | 87 | 97 | 23 |

The above results show that Light-emitting Element 1 fabricated in this example is a high-luminance light-emitting element having high current efficiency. Moreover, as for color purity, the light-emitting element exhibits yellow light emission with excellent color purity.

Figure 14:
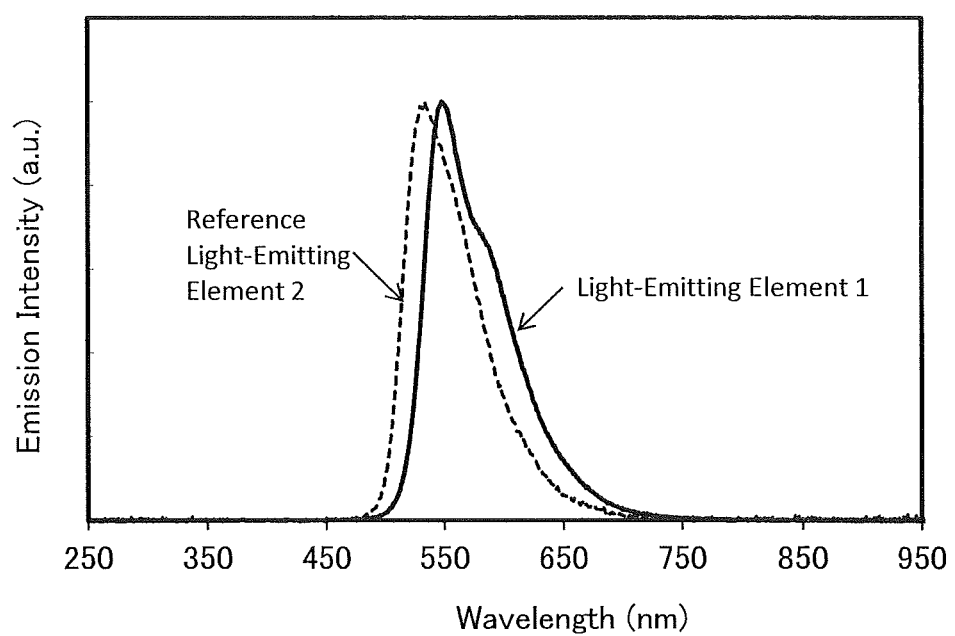
FIG. 14 shows an emission spectrum of Light-emitting Element 1.

FIG. 14 shows emission spectra of Light-emitting Element 1 and Comparative Light-emitting Element 2 to which current was applied at a current density of 25 mA/cm$^2$. As shown in FIG. 14, the emission spectrum of Light-emitting Element 1 has a peak at around 548 nm and it is suggested that the peak is derived from emission of the organometallic iridium complex of one embodiment of the present invention, [Ir(5dppm2)$_2$(acac)]. The emission spectrum of Comparative Light-emitting Element 2 has a peak at around 534 nm and it is suggested that the peak is derived from emission of the organometallic iridium complex [Ir(ppm2-dmp)$_2$(acac)]. As seen from FIG. 14 which shows the emission spectra of the light-emitting elements, an emission spectrum peak of [Ir(5dppm2)$_2$(acac)], which is one embodiment of the present invention, is in a longer wavelength region (i.e., in a yellow emission region) than an emission spectrum peak of [Ir(ppm2-dmp)$_2$(acac)] exhibiting green light emission, which was used for Comparative Light-emitting Element 2. In addition, the emission spectrum of [Ir(5dppm2)$_2$(acac)] is broad (the half width is wide) and has a shoulder peak at around 600 nm which is derived from red light emission. These differences in spectrum are caused by a difference in the dihedral angle between a pyrimidine ring included in a molecular structure of each of [Ir(5dppm2)$_2$(acac)] and [Ir(ppm2-dmp)2(acac) and a phenyl group bonded to the 5-position of the pyrimidine ring. Accordingly, a characteristic spectrum of the organometallic iridium complex of one embodiment of the present invention can be obtained by setting the dihedral angle between a pyrimidine ring and a phenyl group in a stable structure to from −20° to −60° when the organometallic iridium complex is in the singlet ground state ($S_0$) and to from −10° to −50° when the organometallic iridium complex is in the lowest triplet excited state ($T_1$).

Figure 15:
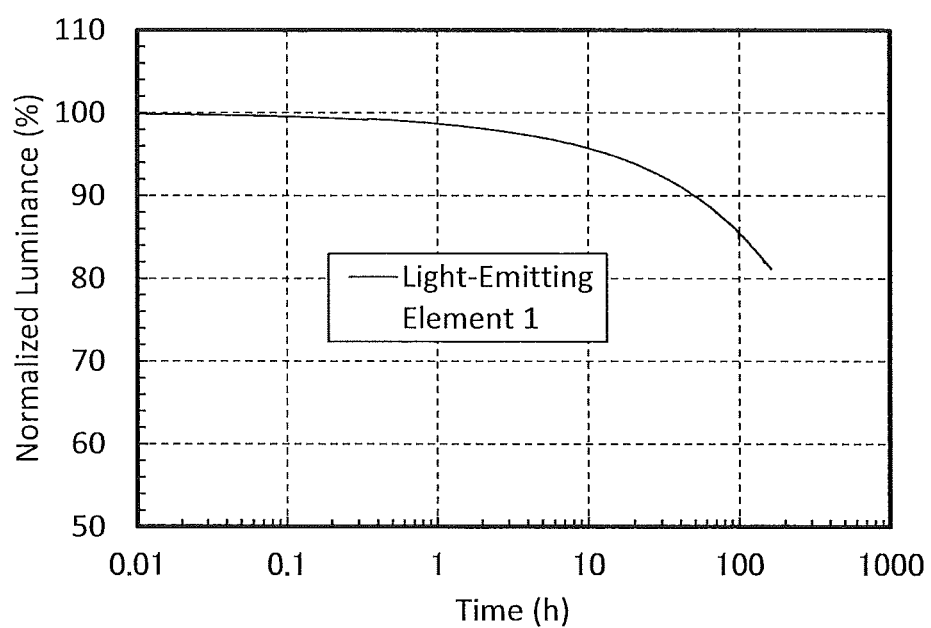
FIG. 15 shows reliability of Light-emitting Element 1.

Light-emitting Element 1 was subjected to a reliability test. FIG. 15 shows the result of the reliability test. In FIG. 15, the vertical axis represents normalized luminance (%) with an initial luminance of 100%, and the horizontal axis represents driving time (hour) of the element. Note that in the reliability test, Light-emitting Element 1 was driven under the conditions where the initial luminance was 5000 cd/m$^2$ and the current density was constant. The result demonstrated that the luminance of Light-emitting Element 1 after 100-hour driving was approximately 85% of the initial luminance.

Thus, the reliability test revealed high reliability of Light-emitting Element 1. In addition, it was confirmed that the use of the organometallic iridium complex of one embodiment of the present invention can provide a long-lifetime light-emitting element.

Example 3

In this example, Light-emitting Elements 3 to 6 each including the organometallic iridium complex of one embodiment of the present invention were fabricated. The element structures are described in detail with reference to FIG. 16. Chemical formulae of materials used in this example are shown below.

-continued
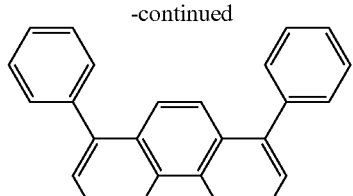
Bphen
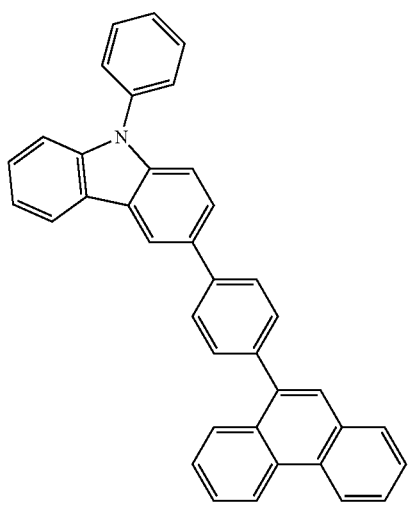
PCPPn
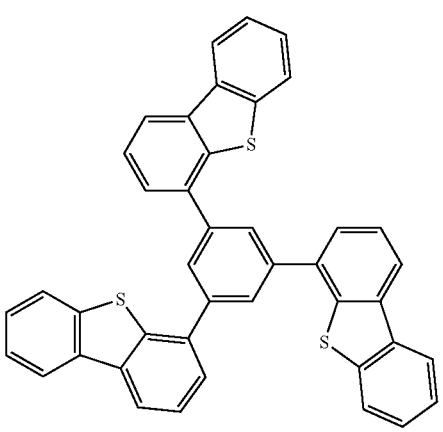
DBT3P-II
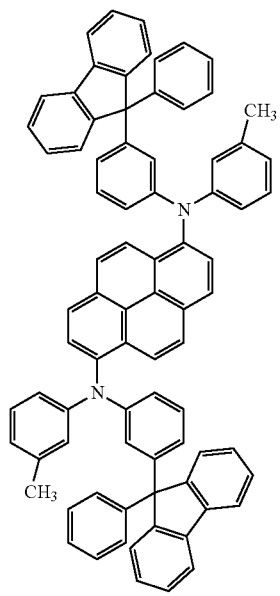
1,6mMemFLPAPrn
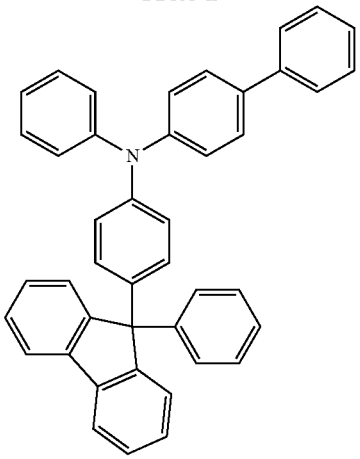
BPAFLP
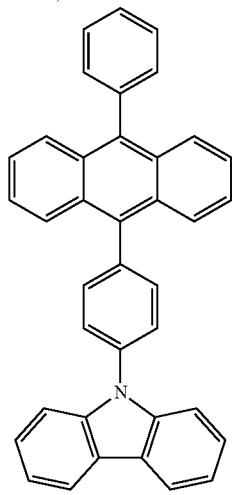
CzPA
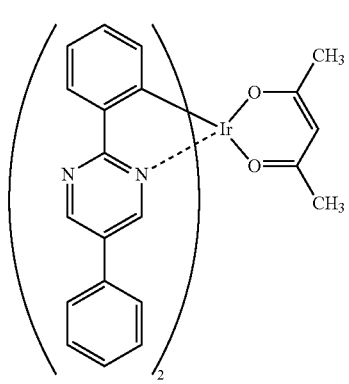
[Ir(5dppm2)$_2$(acac)] (100)

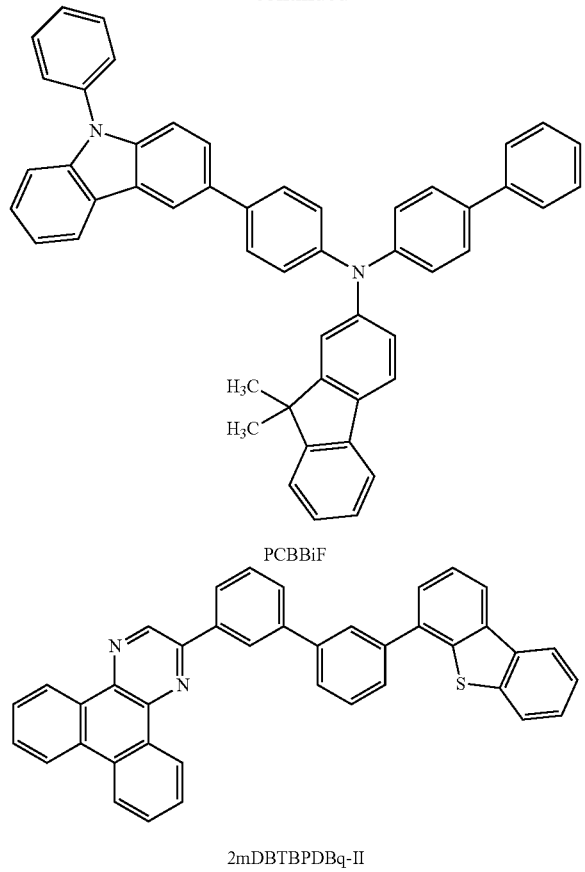

PCBBiF

2mDBTBPDBq-II

<<Fabrication of Light-Emitting Elements 3 to 6>>

Figure 16:
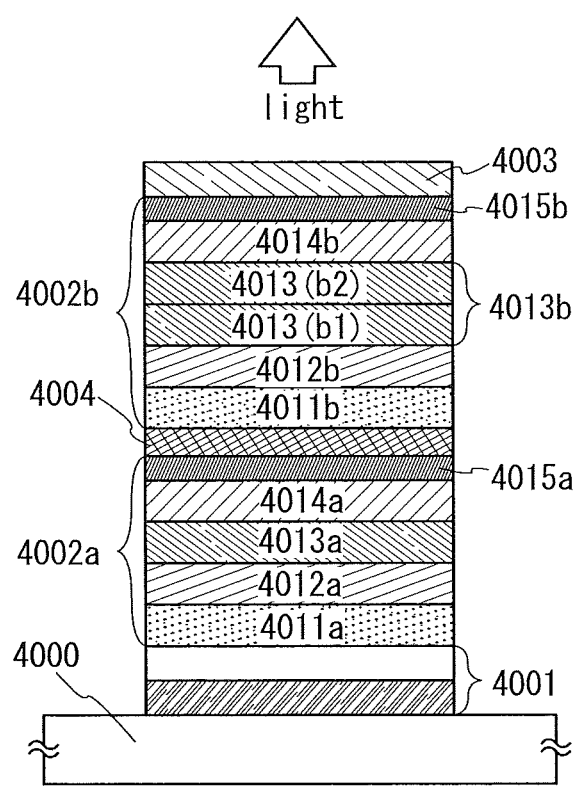
FIG. 16 illustrates a light-emitting element.

FIG. 16 illustrates a stacked structure of each of Light-emitting Elements 3 to 6 to be described in this example. Light-emitting Elements 3 to 6 were optically adjusted so that Light-emitting Element 3 exhibited red light emission, Light-emitting Element 4 exhibited green light emission, Light-emitting Element 5 exhibited blue light emission, and Light-emitting Element 6 exhibited yellow light emission. Specifically, the light-emitting elements were optically adjusted by changing the thicknesses of the first electrode 4001 and the first hole-injection layer 4011a for each light-emitting element. Each of the light-emitting elements has a structure in which light is emitted from the second electrode 4003 side. Although not shown in FIG. 16, a color filter for extracting red light was provided over a second electrode 4003 of Light-emitting Element 3 (above the second electrode 4003 in FIG. 16), a color filter for extracting green light was provided over the second electrode 4003 of Light-emitting Element 4, a color filter for extracting blue light was provided over the second electrode 4003 of Light-emitting Element 5, and a color filter for extracting yellow light was provided over the second electrode 4003 of Light-emitting Element 6. Each light emission can be obtained with high purity.

The first electrode 4001 serves as an anode, which was formed in the following manner. An alloy an of aluminum (Al), nickel (Ni), and lanthanum (La) (Al—Ni—La alloy film) with a thickness of 200 nm was deposited over a glass substrate 4000 by a sputtering method, a film of titanium (Ti) with a thickness of 6 nm was deposited by a sputtering method, and then a film of indium tin oxide containing silicon oxide (ITSO) was deposited by a sputtering method.

The thicknesses of ITSO of Light-emitting Elements 3, 4, 5, and 6 were set to 75 nm, 40 nm, 40 nm, and 10 nm, respectively. At this time, the film of Ti was partially or entirely oxidized and contained titanium oxide. The electrode area was set to 4 mm$^2$ (2 mm×2 mm).

As pretreatment, a surface of the substrate 4000 was washed with water, baking was performed at 200° C. for 1 hour, and then UV ozone treatment was performed for 370 seconds. After that, the substrate was transferred into a vacuum evaporation apparatus where the pressure had been reduced to approximately 10$^{-4}$ Pa, and subjected to vacuum baking at 170° C. in a heating chamber of the vacuum evaporation apparatus for 60 minutes, and then the substrate 4000 was cooled down for approximately 30 minutes.

The first EL layer 4002a, the charge-generation layer 4004, the second EL layer 4002b, and the second electrode 4003 were sequentially formed over the first electrode 4001. The first EL layer 4002a includes the first hole-injection layer 4011a, a first hole-transport layer 4012a, a light-emitting layer (A) 4013a, a first electron-transport layer 4014a, and a first electron-injection layer 4015a. The second EL layer 4002b includes a second hole-injection layer 4011b, a second hole-transport layer 4012b, a light-emitting layer (B) 4013b, a second electron-transport layer 4014b, and a second electron-injection layer 4015b.

After reducing the pressure in the vacuum evaporation apparatus to 10$^{-4}$ Pa, the first hole-injection layer 4011a was formed over the first electrode 4001 by co-evaporation of 9-[4-(9-phenyl-9H-carbazol-3-yl)phenyl]phenanthrene (abbreviation: PCPPn) and molybdenum oxide with a mass ratio of PCPPn to molybdenum oxide being 1:0.5. Note that the co-evaporation method is an evaporation method by which a plurality of different substances is concurrently vaporized from different evaporation sources. The thicknesses of the first hole-injection layer 4011a of Light-emitting Elements 3, 4, 5, and 6 were set to 20 nm, 10 nm, 10 nm, and 25 nm, respectively.

The first hole-transport layer 4012a was formed by evaporation of PCPPn over the first hole-injection layer 4011a. The thicknesses of the first hole-transport layers 4012a of Light-emitting Elements 3, 4, 5, and 6 were 10 nm, 10 nm, 10 nm, and 10 nm, respectively.

The light-emitting layer (A) 4013a was formed over the first hole-transport layer 4012a by co-evaporation of 9-[4-(10-phenyl-9-anthracenyl)phenyl]-9H-Carbazole (abbreviation: CzPA) and N,N'-bis(3-methylphenyl)-N,N'-bis[3-(9-phenyl-9H-fluoren-9-yl)phenyl]pyrene-1,6-diamine (abbreviation: 1,6mMemFLPAPrn) with a mass ratio of CzPA to 1,6mMemFLPAPrn being 1:0.05. The thickness of the light-emitting layer (A) 4013a was set to 25 nm in each of Light-emitting Elements 3 to 6.

The first electron-transport layer 4014a was formed in such a manner that a film of CzPA was formed by evaporation to a thickness of 5 nm over light-emitting layer (A) 4013a and then a film of bathophenanthroline (abbreviation: Bphen) was formed by evaporation to a thickness of 15 nm.

The first electron-injection layer 4015a was formed over the first electron-transport layer 4014a by evaporation of lithium oxide (Li$_2$O) to a thickness of 0.1 nm.

The charge-generation layer 4004 was formed over the first electron-injection layer 4015a by evaporation of copper phthalocyanine (abbreviation: CuPc) to a thickness of 2 nm.

The second hole-injection layer 4011b was formed over the charge-generation layer 4004 by co-evaporation of 1,3,5-tri(dibenzothiophen-4-yl)benzene (abbreviation: DBT3P-II) and molybdenum oxide with a mass ratio of DBT3P-II to molybdenum oxide being 1:0.5. The thickness of the second hole-injection layer 4011b was set to 12.5 nm.

The second hole-transport layer 4012b was formed over the second hole-injection layer 4011b by evaporation of BPAFLP to a thickness of 20 nm.

The light-emitting layer (B) 4013b had a stacked-layer structure of two layers of the first light-emitting layer 4013(b1) and the second light-emitting layer 4013(b2).

The first light-emitting layer 4013(b1) was formed over the second hole-transport layer 4012b by co-evaporation of 2-[3'-(dibenzothiophen-4-yl)biphenyl-3-yl]dibenzo[f,h]quinoxaline (abbreviation: 2mDBTBPDBq-II), N-(1,1'-biphenyl-4-yl)-N-[4-(9-phenyl-9H-carbazol-3-yl)phenyl]-9,9-dimethyl-9H-fluoren-2-amine (abbreviation: PCBBiF), and bis[5-phenyl-2-pyrimidinyl-κN)phenyl-κC](2,4-pentanedionato-κ$^2$O,O')iridium(III) (abbreviation: [Ir(5dppm2)$_2$ (acac)]) with a mass ratio of 2mDBTBPDBq-II to PCBBiF to [Ir(5dppm2)$_2$(acac)] being 0.7:0.3:0.06. The thickness of the first light-emitting layer 4013(b1) was set to 20 nm.

The second light-emitting layer 4013(b2) was formed over the first light-emitting layer 4013(b1) by co-evaporation of 2mDBTBPDBq-II and [Ir(5dppm2)$_2$(acac)] with a mass ratio of 2mDBTBPDBq-II to [Ir(5dppm2)$_2$(acac)] being 1:0.06. The thickness of the second light-emitting layer 4013(b2) was set to 20 nm.

The second electron-transport layer 4014b was formed in such a manner that 2mDBTPDBq-II was deposited by evaporation over the second light-emitting layer 4013(b2) to a thickness of 20 nm and then Bphen was deposited by evaporation to a thickness of 20 nm.

The second electron-injection layer 4015b was formed over the second electron-transport layer 4014b by evaporation of lithium fluoride (LiF) to a thickness of 1 nm.

The second electrode 4003 was an electrode serving as a cathode and formed in such a manner that silver (Ag) and magnesium (Mg) were deposited by co-evaporation at a mass ratio of 1:0.1 to a thickness of 15 nm over the second electron-injection layer 4015b, and then indium tin oxide (ITO) was deposited to a thickness of 70 nm by a sputtering method. Note that an evaporation method using resistive heating was employed for all the evaporation steps.

Although not shown in FIG. 16, the color filters (coloring layers) provided for Light-emitting Elements 3 to 6 were formed over a counter substrate. The light-emitting elements formed over the substrate 4000 were positioned so as to overlap with the color filters. Then, the substrate and the counter substrate were bonded and the light-emitting elements were sealed in a glove box containing a nitrogen atmosphere so as not to be exposed to the air (specifically, a sealant was applied to surround each element, and irradiation with ultraviolet light with a wavelength of 365 nm at 6 J/cm$^2$ and heat treatment at 80° C. for 1 hour were performed for sealing).

Table 3 shows element structures of Light-emitting Elements 3 to 6 obtained through the above steps.

TABLE 3

| | | Light-emitting Element 3(R) | Light-emitting Element 4(G) | Light-emitting Element 5(B) | Light-emitting Element 6(Y) |
|---|---|---|---|---|---|
| | CF | R (2.36 μm) | G (1.29 μm) | B (0.78 μm) | Y (0.80 μm) |
| | Second electrode | ITO (70 nm) | | | |
| | | Ag:Mg (1:0.1 15 nm) | | | |
| | Second electron-injection layer | LiF (1 nm) | | | |
| | Second electron-transport layer | Bphen (20 nm) | | | |
| | | 2mDBTBPDBq-II (20 nm) | | | |
| Light-emitting layer (B) | Second light-emitting layer | *3 | | | |
| | First light-emitting layer | *2 | | | |
| | Second hole-transport layer | BPAFLP (20 nm) | | | |
| | Second hole-injection layer | DBT3P-II:MoOx | | | |
| | | (1:0.05 12.5 nm) | | | |
| | Charge generation layer | CuPc (2 nm) | | | |
| | First electron-injection layer | Li$_2$O (0.1 nm) | | | |
| | First electron-transport layer | Bphen (15 nm) | | | |
| | | CzPA (5 nm) | | | |
| | Light-emitting layer (A) | *1 | | | |
| | First hole-transport layer | PCPPn (10 nm) | | | |
| | First hole-injection layer | PCPPn:MoOx (1:0.5 20 nm) | PCPPn:MoOx (1:0.5 10 nm) | PCPPn:MoOx (1:0.5 10 nm) | PCPPn:MoOx (1:0.5 25 nm) |
| | First electrode | NITO (75 nm) | NITO (40 nm) | NITO (40 nm) | NITO (10 nm) |
| | | | Al—Ni—La\Ti (200 nm\6 nm) | | |

*1 CzPA:1,6mMemFLPAPrn (1:0.05 *1 = 25 nm)
*2 2mDBTBPDBq-II:PCBBiF:[Ir(5dppm2)$_2$(acac)] (0.7:0.3:0.06 20 nm)
*3 2mDBTBPDBq-II:[Ir(5dppm2)$_2$(acac)] (1:0.06 20 nm)

<<Operation Characteristics of Light-Emitting Elements 3 to 6>>

Figure 17:
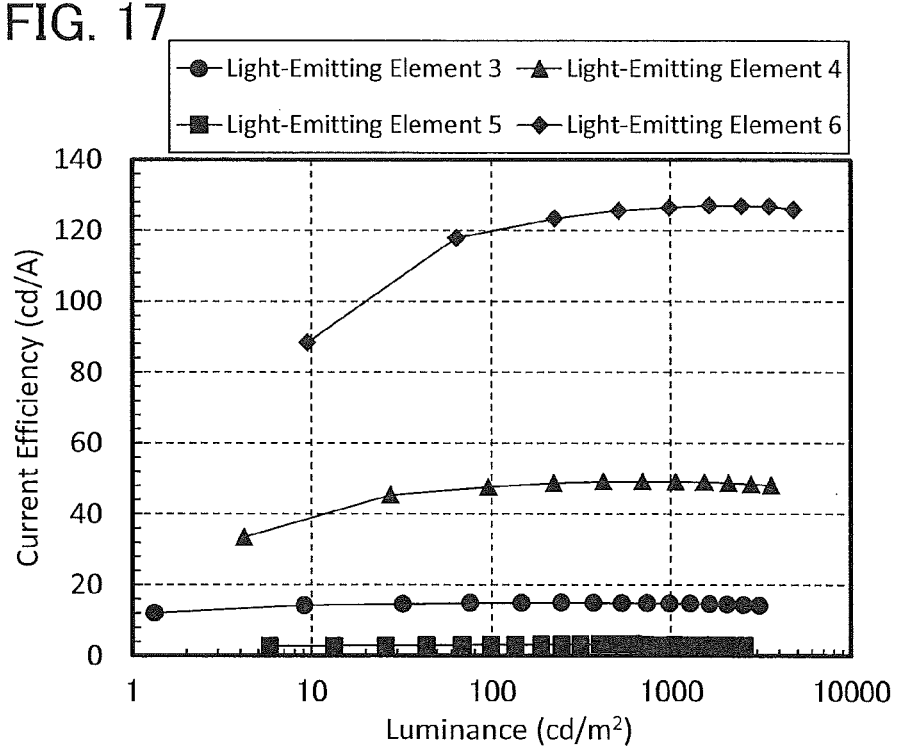
FIG. 17 shows luminance-current efficiency characteristics of Light-emitting Elements 3 to 6.
Figure 18:
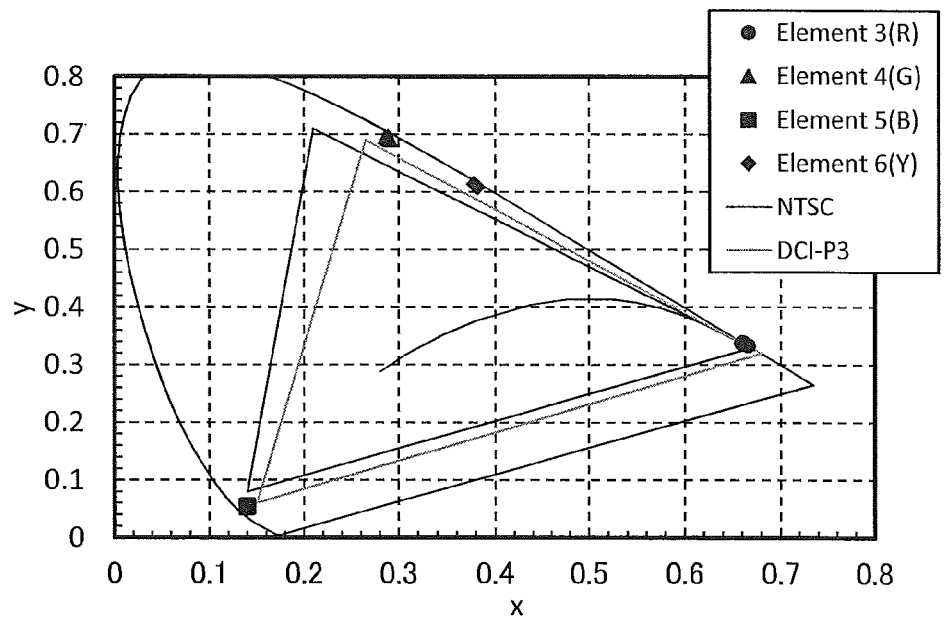
FIG. 18 shows chromaticity characteristics of Light-emitting Elements 3 to 6.
Figure 19:
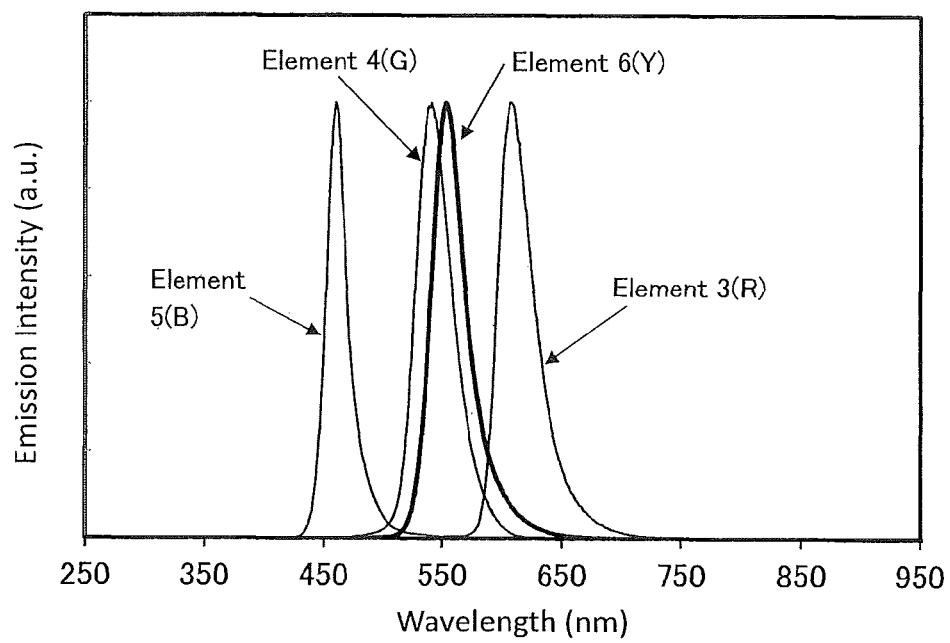
FIG. 19 shows emission spectra of Light-emitting Elements 3 to 6.

Operation characteristics of Light-emitting Elements 3 to 6 were evaluated. The measurement was performed at room temperature (in an atmosphere kept at 25° C.). FIG. 17 to FIG. 19 show the results.

Table 4 shows initial main characteristics of Light-emitting Elements 3 to 6 at a luminance of about 1000 cd/m².

TABLE 4

| | Voltage (V) | Chromaticity (x, y) | Luminance (cd/m²) | Current efficiency (cd/A) | Power efficiency (lm/W) |
|---|---|---|---|---|---|
| Light-emitting Element 3 (R) | 6.8 | (0.67, 0.34) | 980 | 15 | 6.9 |
| Light-emitting Element 4 (G) | 6.2 | (0.29, 0.69) | 1100 | 49 | 25 |
| Light-emitting Element 5 (B) | 8.4 | (0.14, 0.05) | 1000 | 3.1 | 1.2 |
| Light-emitting Element 6 (Y) | 5.8 | (0.38, 0.61) | 980 | 130 | 69 |

The above results are summarized as follows. Light-emitting Element 3 fabricated in this example has high current efficiency and can provide red light emission having high color purity close to the red-color chromaticity defined by the national television standards committee (NTSC). Light-emitting Element 4 has high current efficiency and can provide green light emission having high current efficiency and high color purity close to the green-color chromaticity defined by NTSC. Light-emitting Element 5 has high current efficiency and can provide blue light emission having high color purity close to the blue-color chromaticity defined by NTSC. Light-emitting Element 6 has high current efficiency and can provide yellow light emission having high color purity close to the yellow-color chromaticity defined by NTSC.

FIG. 19 shows emission spectra when a current at a current density of 2.5 mA/cm² was supplied to Light-emitting Elements 3 to 6. As shown in FIG. 19, the emission spectrum of Light-emitting Element 3 which exhibits red light emission has a peak at around 606 nm, the emission spectrum of Light-emitting Element 4 which exhibits green light emission has a peak at around 542 nm, and the emission spectrum of Light-emitting Element 5 which exhibits blue light emission has a peak at around 460 nm. Each of Light-emitting Elements 3 to 5 has a narrow emission spectrum. In contrast, the emission spectrum of Light-emitting Element 6 which exhibits yellow light emission is broad and has a peak at around 553 nm.

Light-emitting Elements 3 to 6 described in this example were formed over the same substrate. Each of Light-emitting Elements 3 to 6 was optically adjusted so that the optical path length from the second electrode to the interface between the first light-emitting layer 4013(*b*1) and the second light-emitting layer 4013(*b*2) included in the light-emitting layer (B) was less than λ/4. The above results show that such an element structure allows Light-emitting Elements 3, 4, 5, and 6 over the same substrate to exhibit red, green, blue, and yellow light emission, respectively, with high color purity based on the NTSC standard.

Example 4

In this example, in each of the organometallic iridium complex of one embodiment of the present invention, [Ir(5dppm2)₂(acac)] (Structural Formula (100)) shown below and the organometallic iridium complex used for comparison, [Ir(ppm2-dmp)₂(acac)] (Structural Formula (200)), the dihedral angle between a pyrimidine ring (Pm) and a phenyl group (Ph) bonded to the 5-position of the pyrimidine ring (Pm) was calculated. In the case where atoms 1 to 4 in the structural formulae are bonded in this order, the dihedral angle is an angle formed by a plane faulted by the atoms 1 to 3 and a plane formed by the atoms 2 to 4 which rotate around a bond axis formed between the atoms 2 and 3.

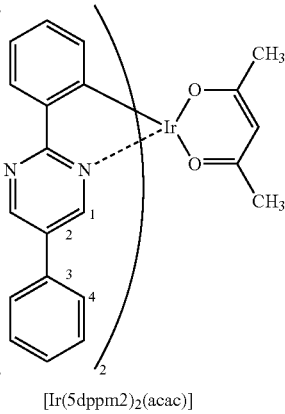

[Ir(5dppm2)₂(acac)]

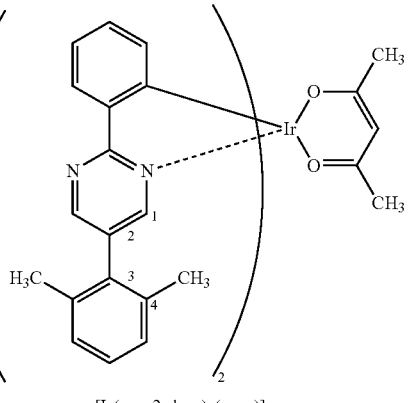

[Ir(ppm2-dmp)₂(acac)]

First, stable structures of [Ir(5dppm2)₂(acac)] and [Ir(ppm2-dmp)₂(acac)] in the singlet ground state (S₀) and the lowest triplet excited state (T₁) were calculated using the density functional theory (DFT). In the DFT, the total energy is represented as the sum of potential energy, electrostatic energy between electrons, electronic kinetic energy, and exchange-correlation energy including all the complicated interactions between electrons. Also in the DFT, since an exchange-correlation interaction is approximated by a functional (a function of another function) of one electron potential represented in terms of electron density, calculations are performed at high speed. Here, B3PW91, which is a hybrid functional, was used to specify the weight of each parameter related to exchange-correlation energy.

As basis functions, 6-311G (a basis function of a triple-split valence basis set using three contraction functions for a valence orbital) was applied to each of H, C, N, and O atoms, and LanL2DZ was applied to an Ir atom. By the above basis function, for example, orbits of 1s to 3s are considered in the case of hydrogen atoms while orbits of 1s to 4s and 2p to 4p are considered in the case of carbon atoms.

Furthermore, to improve calculation accuracy, the p function and the d function, respectively, were added as polarization basis sets to hydrogen atoms and atoms other than hydrogen atoms. To take solvent effects into calculation, integral equation formalism polarizable continuum model (IEF-PCM) was used. Dichloromethane was used as a developing solvent.

Note that Gaussian 09 was used as a quantum chemistry computational program. A high performance computer (manufactured by SGI Japan, Ltd.) was used for the calculation.

Table 5 shows the calculation results of the dihedral angle between a pyrimidine ring (Pm) and a phenyl group (Ph) bonded to the 5-position of the pyrimidine ring (Pm) in stable structures of [Ir(5dppm2)$_2$(acac)] and [Ir(ppm2-dmp)$_2$(acac)] in the singlet ground state (S$_0$) and the lowest triplet excited state (T$_1$).

TABLE 5

|  | [Ir(5dppm2)$_2$(acac)] | [Ir(ppm2-dmp)$_2$(acac)] |
| --- | --- | --- |
| S$_0$ | −38.3° | −89.2° |
| T$_1$ | −24.0° | −69.1° |

As shown in Table 5, [Ir(ppm2-dmp)$_2$(acac)] in the S$_0$ state and in the T$_1$ state has a larger dihedral angle between a pyrimidine ring and a phenyl group bonded to the 5-position of the pyrimidine ring than [Ir(5dppm2)$_2$(acac)] in the S$_0$ state and in the T$_1$ state does. This is because introduction of a methyl group causes steric hindrance between the pyrimidine ring and the phenyl group bonded to the 5-position of the pyrimidine ring. The large twist between the pyrimidine ring and the phenyl group bonded to the 5-position of the pyrimidine ring inhibits extension of π-conjugation. Therefore, the organometallic iridium complex with a twist structure has a peak wavelength of an emission spectrum on a short wavelength side.

In the iridium complex which includes a ligand in which a first phenyl group and a second phenyl group are bonded to a pyrimidine ring and the first phenyl group is bonded to iridium, by setting the dihedral angle between the pyrimidine ring and the second phenyl group to from −20° to −60° when the organometallic iridium complex is in the singlet ground state (S$_0$), and to from −10° to −50° when the organometallic iridium complex is in the lowest triplet excited state (T$_1$), yellow light emission whose peak wavelength of an emission spectrum is at around 560 nm (specifically, in the range of 550 nm to 580 nm) can be obtained. The organometallic iridium complex of one embodiment of the present invention in which the dihedral angle is in the above range has a broad emission spectrum and a shoulder peak at around 600 nm (specifically, in the range of 570 nm to 630 nm) which is derived from red light emission.

Example 5

Synthetic Example 2

In this example, described is a method for synthesizing bis{2-[5-(2,6-dimethylphenyl)-2-pyrimidinyl-κN]phenyl-κC}(2,4-pentanedionato-κ$^2$O,O')iridium(III) (abbreviation: [Ir(ppm2-dmp)$_2$(acac)]), which is the organometallic iridium complex represented by Structural Formula (200) in Example 2. The structure of [Ir(ppm2-dmp)$_2$(acac)] is shown below.

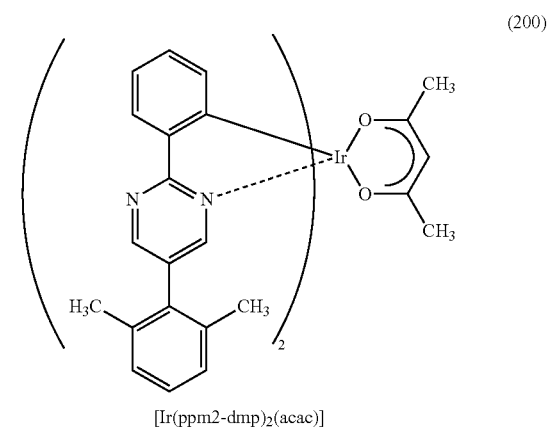

[Ir(ppm2-dmp)$_2$(acac)]

Step 1: Synthesis of 5-bromo-2-phenylpyrimidine

First, 1.97 g of 5-bromo-2-iodopyrimidine, 0.85 g of phenylboronic acid, 7.0 mL of a 2M sodium carbonate aqueous solution, and 18 mL of toluene were put in a 200-mL three-neck flask equipped with a reflux pipe, and the atmosphere in the flask was replaced with nitrogen. After the mixture was degassed by being stirred under reduced pressure, 0.081 g of tetrakis(triphenylphosphine)palladium(0) (abbreviation: Pd(PPh$_3$)$_4$) was added thereto and the mixture was refluxed for 8 hours. Here, 0.040 g of Pd(PPh$_3$)$_4$ was added and the mixture was refluxed for 8 hours, and then, 0.040 g of Pd(PPh$_3$)$_4$ was further added and the mixture was further refluxed for 8 hours to cause a reaction. Water was added to the resulted solution, and an organic layer was extracted with dichloromethane. The obtained solution of the extract was washed with saturated brine, and magnesium sulfate was added for drying. The solution obtained by the drying was filtrated. The solvent of this solution was distilled off, and then the obtained residue was purified by flash column chromatography using hexane and ethyl acetate as a developing solvent in a ratio of 5:1, so that the objective pyrimidine derivative (white powder) was obtained in a yield of 59%). A synthetic scheme of Step 1 is shown in (b-1) below.

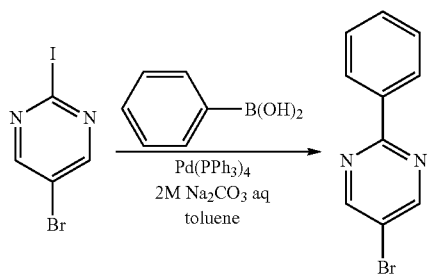

(b-1)

Step 2: Synthesis of 5-(2,6-dimethylphenyl)-2-phenylpyrimidine (Abbreviation: Hppm2-dmp)

Next, 0.96 g of 5-bromo-2-phenylpyrimidine obtained through Step 1, 1.21 g of 2,6-dimethylphenylboronic acid, 0.87 g of sodium carbonate, 0.035 g of bis(triphenylphosphine)palladium(II)dichloride (abbreviation: $Pd(PPh_3)_2Cl_2$), 15 mL of water, and 15 mL of acetonitrile were put in a recovery flask equipped with a reflux pipe, and the mixture was bubbled with argon for 15 minutes. This reaction container was heated by irradiation with microwaves (2.45 GHz, 100 W) for 3 hours. Here, 1.21 g of 2,6-dimethylphenylboronic acid, 0.87 g of sodium carbonate, and 0.035 g of $Pd(PPh_3)_2Cl_2$ were added to the flask, and the mixture was bubbled with argon for 15 minutes. This reaction container was heated again by irradiation with microwaves (2.45 GHz, 100 W) for 3 hours. After that, the obtained mixture was suction-filtered with water. The obtained solid was purified by flash column chromatography using toluene as a developing solvent, so that Hdmppm2-dmp (white powder), which was an objective pyrimidine derivative, was obtained in a yield of 64%. Note that a microwave synthesis system (Discover, manufactured by CEM Corporation) was used for the irradiation with microwaves. A synthetic scheme of Step 2 is shown in (b-2) below.

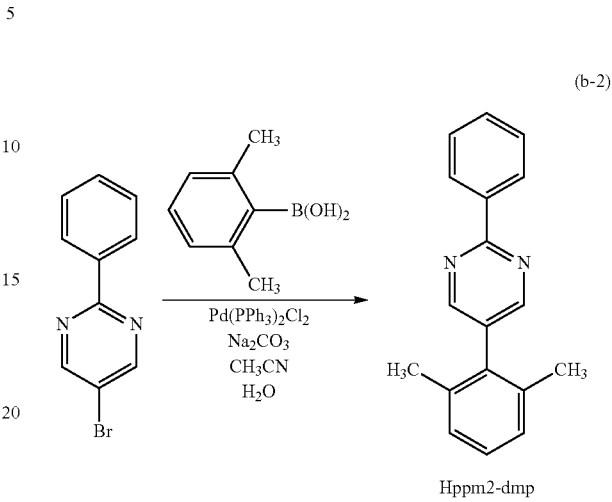

Step 3: Synthesis of di-μ-chloro-tetrakis{2-[5-(2,6-dimethylphenyl)-2-pyrimidinyl-κN]phenyl-κC}diiridium(III) (Abbreviation: [Ir(ppm2-dmp)$_2$Cl]$_2$)

Next, 15 mL of 2-ethoxyethanol, 5 mL of water, 0.68 g of Hppm2-dmp obtained through Step 2, and 0.36 g of iridium chloride hydrate (IrCl$_3$.H$_2$O) (produced by Sigma-Aldrich Corporation) were put in a recovery flask equipped with a reflux pipe, and the atmosphere in the flask was replaced with argon. After that, irradiation with microwaves (2.45 GHz, 100 W) was performed for 1 hour to cause a reaction. The solvent was distilled off, and then the obtained residue was suction-filtered and washed with hexane to give a dinuclear complex [Ir(ppm2-dmp)$_2$Cl]$_2$ (yellow-brown powder) in a yield of 53%. A synthetic scheme of Step 3 is shown in (b-3) below.

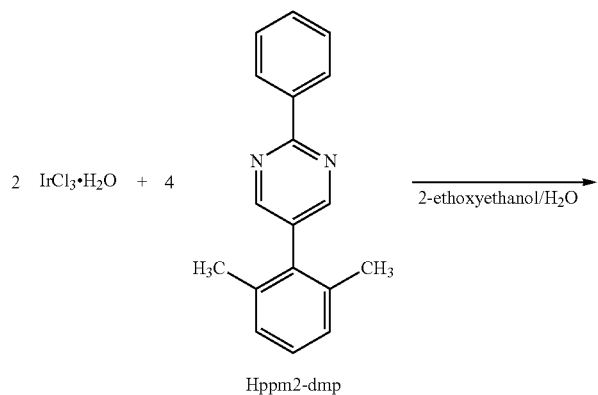

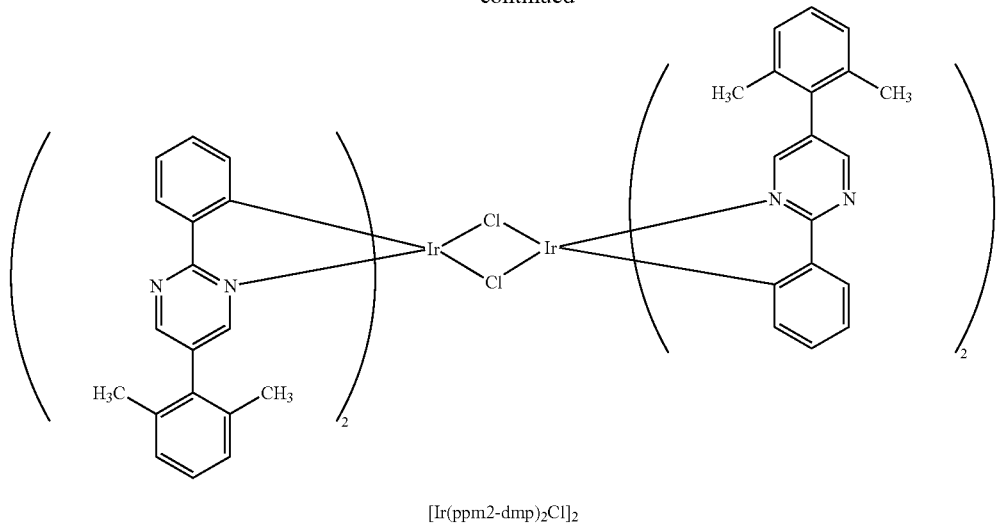

[Ir(ppm2-dmp)₂Cl]₂

Step 4: Synthesis of bis{2-[5-(2,6-dimethylphenyl)-2-pyrimidinyl-κN]phenyl-κC}(2,4-pentanedionato-κ²O,O')iridium(III) (Abbreviation: [Ir(ppm2-dmp)₂(acac)])

In a recovery flask equipped with a reflux pipe were put 20 mL of 2-ethoxyethanol, 0.48 g of the dinuclear complex [Ir(ppm2-dmp)₂Cl]₂ obtained through Step 3, 0.094 g of acetylacetone (abbreviation: Hacac), and 0.34 g of sodium carbonate, and the atmosphere in the flask was replaced with argon. Then, irradiation with microwaves (2.45 GHz, 120 W) was performed for 60 minutes. Here, 0.094 g of Hacac was further added, and the mixture was heated by irradiation with microwaves (2.45 GHz, 200 W) for 60 minutes. The solvent was distilled off, and the obtained residue was suction-filtered with hexane. The obtained solid was washed with water and washed with and hexane. The obtained solid was purified by flash column chromatography using hexane and ethyl acetate as a developing solvent in a ratio of 5:1, and then recrystallization was performed with a mixed solvent of dichloromethane and hexane; thus, organometallic the complex [Ir(ppm2-dmp)₂(acac)] was obtained in a yield of 58%. A synthetic scheme of Step 4 is shown in (b-4) below.

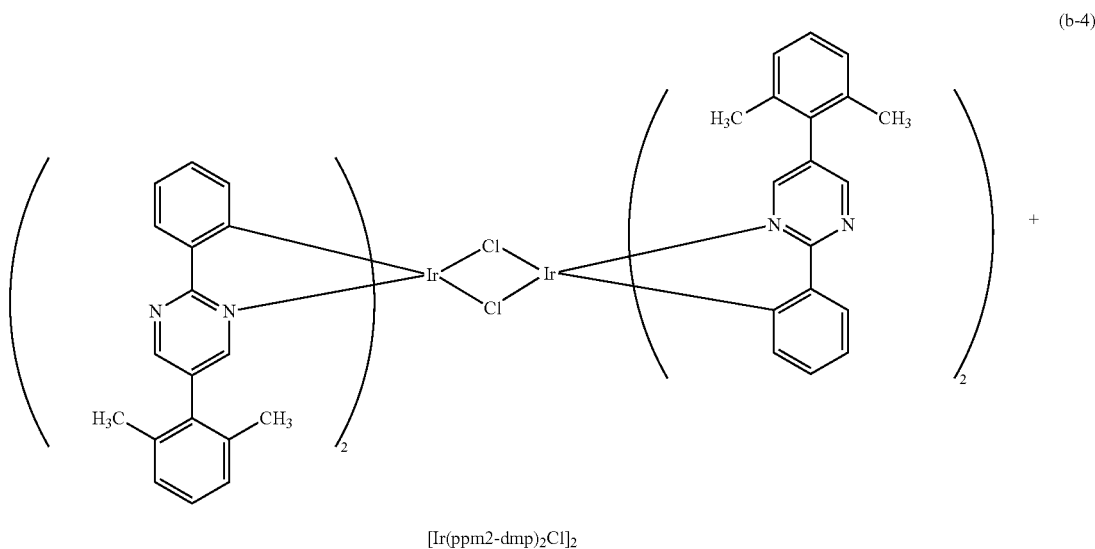

(b-4)

[Ir(ppm2-dmp)₂Cl]₂

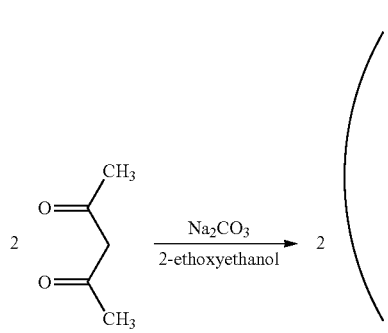 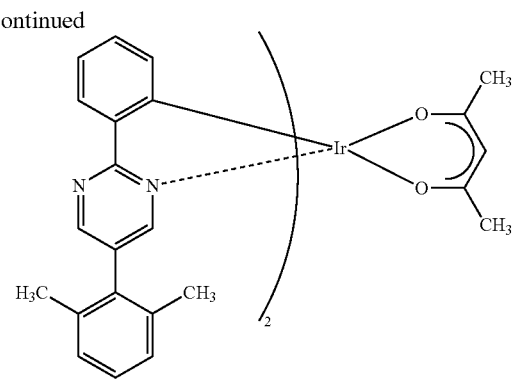

[Ir(ppm2-dmp)₂(acac)]
(200)

Figure 20:
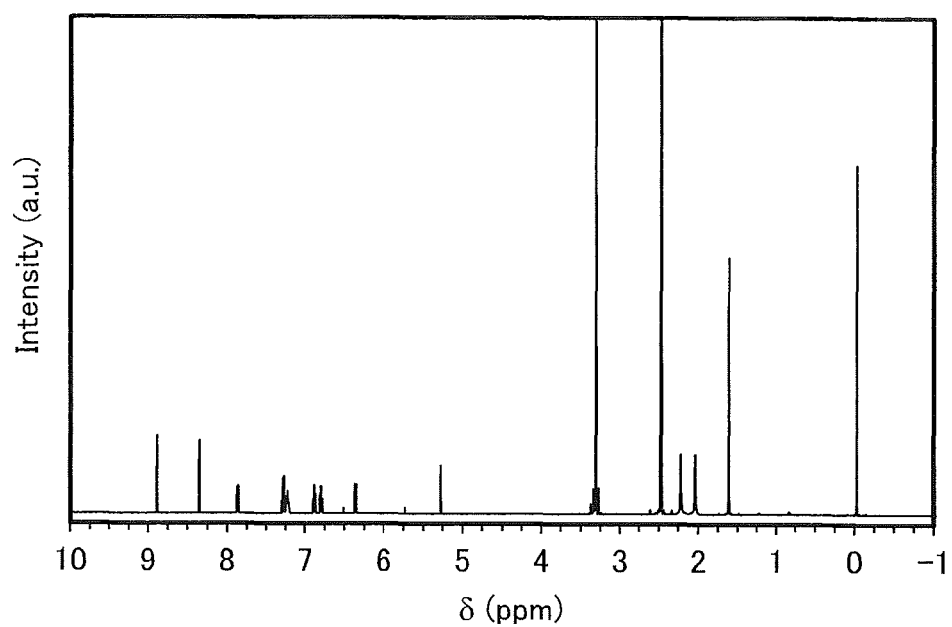
FIG. 20 is a $^1$H-NMR chart of an organometallic iridium complex represented by Structural Formula (200).

An analysis result by nuclear magnetic resonance spectroscopy (¹H-NMR) of the yellow powder obtained through Step 4 is shown below. FIG. 20 is a ¹H-NMR chart. This result reveals that [Ir(ppm2-dmp)₂(acac)], which is the organometallic iridium complex of one embodiment of the present invention represented by Structural Formula (200), was obtained in Synthesis example 2.

¹H-NMR. δ (DMSO-d₆): 1.64 (s, 6H), 2.07 (s, 6H), 2.25 (s, 6H), 5.30 (s, 1H), 6.39 (d, 2H), 6.83 (t, 2H), 6.91 (t, 2H), 7.24-7.27 (m, 4H), 7.31 (t, 2H), 7.90 (d, 2H), 8.38 (d, 2H), 8.91 (d, 2H).

Figure 21:
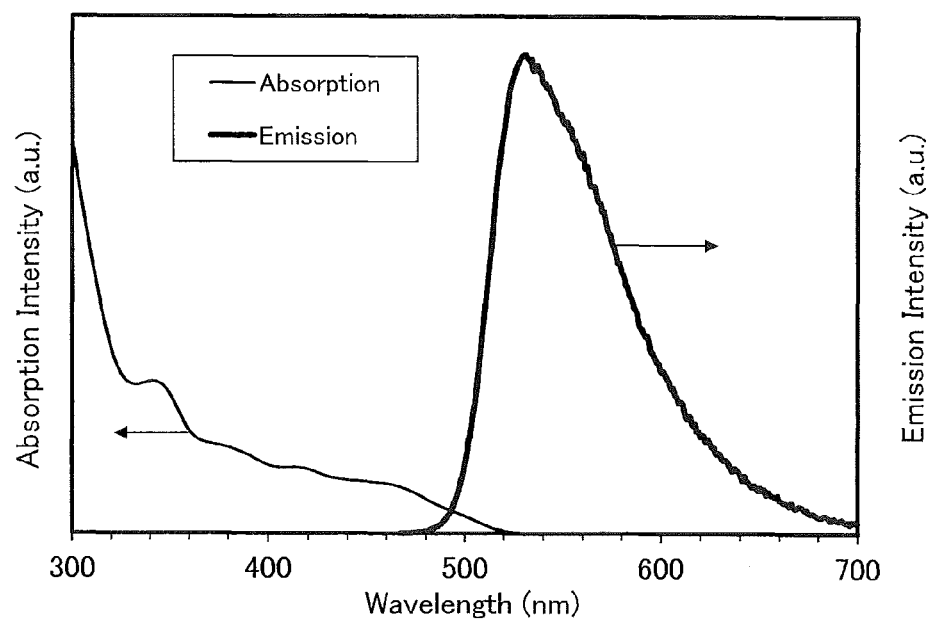
FIG. 21 shows an ultraviolet-visible absorption spectrum and an emission spectrum of an organometallic iridium complex represented by Structural Formula (200).

Next, an ultraviolet-visible absorption spectrum (hereinafter, simply referred to as an "absorption spectrum") and an emission spectrum of a dichloromethane solution of [Ir(ppm2-dmp)₂(acac)] were measured. The measurement of the absorption spectrum was conducted at room temperature, for which an ultraviolet-visible light spectrophotometer (V550 type manufactured by JASCO Corporation) was used and the dichloromethane solution (0.086 mmol/L) was put in a quartz cell. In addition, the measurement of the emission spectrum was conducted at room temperature, for which a fluorescence spectrophotometer (FS920 manufactured by Hamamatsu Photonics K.K.) was used and the degassed dichloromethane solution (0.086 mmol/L) was put in a quartz cell. Measurement results of the obtained absorption and emission spectra are shown in FIG. 21, in which the horizontal axis represents wavelength and the vertical axes represent absorption intensity and emission intensity. In FIG. 21 where there are two solid lines, the thin line represents the absorption spectrum and the thick line represents the emission spectrum. Note that the absorption spectrum in FIG. 21 is the results obtained in such a way that the absorption spectrum measured by putting only dichloromethane in a quartz cell was subtracted from the absorption spectrum measured by putting the dichloromethane solution (0.086 mmol/L) in a quartz cell.

As shown in FIG. 21, the organometallic iridium complex [Ir(ppm2-dmp)₂(acac)] has an emission peak at 531 nm, and green light emission was observed from the dichloromethane solution.

This application is based on Japanese Patent Application serial no. 2014-112278 filed with Japan Patent Office on May 30, 2014, the entire contents of which are hereby incorporated by reference.

What is claimed is:

1. A compound comprising:
a pyrimidine ring; and
a first phenyl group and a second phenyl group each bonded to the pyrimidine ring,
wherein the first phenyl group is bonded to an iridium atom,
wherein the pyrimidine ring is bonded to the iridium atom by a coordinate bond,
wherein a dihedral angle between the pyrimidine ring and the second phenyl group is from −20° to −60° in a stable structure of the compound when the compound is in a singlet ground state,
wherein the dihedral angle is from −10° to −50° in a stable structure of the compound when the compound is in a lowest triplet excited state,
wherein the first phenyl group is bonded to a 2-position of the pyrimidine ring, and
wherein the second phenyl group is bonded to a 5-position of the pyrimidine ring.

2. The compound according to claim 1, wherein an emission spectrum of the compound has a first peak in a range of 550 nm to 580 nm and a second peak in a range of 570 nm to 630 nm.

3. A light-emitting element comprising:
a first electrode and a second electrode; and
an electroluminescent layer between the first electrode and the second electrode,
wherein the electroluminescent layer comprises the compound according to claim 1.

4. A light-emitting device comprising:
the light-emitting element according to claim 3; and
a transistor electrically connected to the light-emitting element.

5. An electronic device comprising:
the light-emitting device according to claim 4; and
at least one of a microphone, a camera, an operation button, an external connection port, and a speaker.

6. A lighting device comprising:
the light-emitting element according to claim 3; and
a support base,
wherein the light-emitting element is over the support base.

7. A light-emitting element comprising:
a first electrode and a second electrode; and
a light-emitting layer between the first electrode and the second electrode, wherein the light-emitting layer comprises the compound according to claim 1.

8. The light-emitting element according to claim 7, wherein the light-emitting layer comprises a first organic compound and a second organic compound.

9. A compound comprising a structure represented by General Formula (G1):

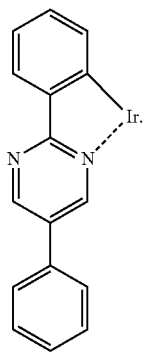

(G1)

10. The compound according to claim 9, the compound represented by General Formula (G2):

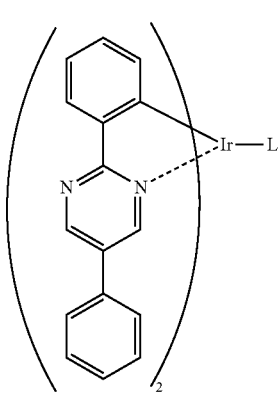

(G2)

wherein L represents a monoanionic ligand.

11. The compound according to claim 10, wherein the monoanionic ligand is a monoanionic bidentate chelate ligand in which two ligand elements are both oxygen or nitrogen.

12. The compound according to claim 10, wherein the monoanionic ligand is represented by General Formula (L1) or (L2):

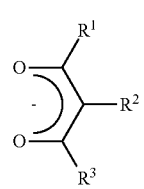

(L1)

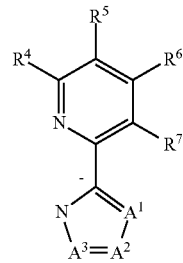

(L2)

wherein each of $R^1$ to $R^7$ independently represents hydrogen, a substituted or unsubstituted alkyl group having 1 to 6 carbon atoms, a halogen group, a vinyl group, a substituted or unsubstituted haloalkyl group having 1 to 6 carbon atoms, a substituted or unsubstituted alkoxy group having 1 to 6 carbon atoms, or a substituted or unsubstituted alkylthio group having 1 to 6 carbon atoms, wherein each of $A^1$ to $A^3$ independently represents nitrogen, sp2 hybridized carbon bonded to hydrogen, or sp2 hybridized carbon having a substituent, and wherein the substituent represents an alkyl group having 1 to 6 carbon atoms, a halogen group, a haloalkyl group having 1 to 6 carbon atoms, or a phenyl group.

13. The compound according to claim 9, the compound represented by Structural Formula (100):

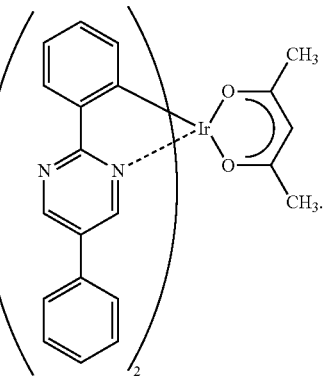

(100)

14. The compound according to claim 9, wherein an emission spectrum of the compound has a first peak in a range of 550 nm to 580 nm and a second peak in a range of 570 nm to 630 nm.

15. A light-emitting element comprising:
a first electrode and a second electrode; and
an electroluminescent layer between the first electrode and the second electrode,
wherein the electroluminescent layer comprises the compound according to claim 9.

16. A light-emitting device comprising:
the light-emitting element according to claim 15; and
a transistor electrically connected to the light-emitting element.

17. An electronic device comprising:
the light-emitting device according to claim 16; and
at least one of a microphone, a camera, an operation button, an external connection port, and a speaker.

18. A lighting device comprising:
the light-emitting element according to claim 15; and
a support base,
wherein the light-emitting element is over the support base.

19. A light-emitting element comprising:
a first electrode and a second electrode; and
a light-emitting layer between the first electrode and the second electrode,
wherein the light-emitting layer comprises the compound according to claim 9.

20. The light-emitting element according to claim 19, wherein the light-emitting layer comprises a first organic compound and a second organic compound.

* * * * *